United States Patent
Bak et al.

(10) Patent No.: US 10,342,876 B2
(45) Date of Patent: Jul. 9, 2019

(54) PROCESS FOR REDUCING SUBVISIBLE PARTICLES IN A PHARMACEUTICAL FORMULATION

(71) Applicant: Regeneron Pharmaceuticals, Inc., Tarrytown, NY (US)

(72) Inventors: Hanne Bak, New York, NY (US); John Mattila, Nyack, NY (US); Ning Li, NewCanaan, CT (US); Xiaolin Tang, Old Tappan, NJ (US); Daniel Dix, LaGrangeville, NY (US); Chen Li, White Plains, NJ (US); William Markis, Passaic, NJ (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 301 days.

(21) Appl. No.: 14/878,079

(22) Filed: Oct. 8, 2015

(65) Prior Publication Data

US 2016/0101181 A1   Apr. 14, 2016

Related U.S. Application Data

(60) Provisional application No. 62/061,797, filed on Oct. 9, 2014.

(51) Int. Cl.
- *A61K 39/395* (2006.01)
- *A61K 47/22* (2006.01)
- *A61K 47/26* (2006.01)

(52) U.S. Cl.
CPC ........ *A61K 47/22* (2013.01); *A61K 39/39591* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 7,427,659 B2 | 9/2008 | Shukla | |
| 7,666,413 B2 | 2/2010 | Liu et al. | |
| 8,491,904 B2 | 7/2013 | Hickman | |
| 9,249,182 B2* | 2/2016 | Herigstad | C07K 16/00 |
| 2010/0136025 A1 | 6/2010 | Hickman | |
| 2010/0278822 A1 | 11/2010 | Fraunhofer et al. | |
| 2013/0131318 A1 | 5/2013 | Kremer | |
| 2014/0046038 A1 | 2/2014 | Ishihara | |
| 2014/0072585 A1 | 3/2014 | Herigstad et al. | |
| 2016/0319012 A1 | 11/2016 | Yu et al. | |
| 2016/0320391 A1 | 11/2016 | Gunawan et al. | |

FOREIGN PATENT DOCUMENTS

| | | | |
|---|---|---|---|
| WO | 2007110339 A1 | 10/2007 | |
| WO | 2009058769 A1 | 5/2009 | |
| WO | 2011098526 A1 | 8/2011 | |
| WO | 2012030512 A1 | 3/2012 | |
| WO | 2012065072 A2 | 5/2012 | |
| WO | 2013066707 A1 | 5/2013 | |
| WO | 2013078170 A1 | 5/2013 | |
| WO | 2013176754 A1 | 11/2013 | |
| WO | 2013177115 A2 | 11/2013 | |
| WO | 2013177118 A2 | 11/2013 | |
| WO | 2014100143 A2 | 6/2014 | |
| WO | 2014143185 A1 | 9/2014 | |
| WO | 2014145208 A1 | 9/2014 | |
| WO | 2015038888 A1 | 3/2015 | |

OTHER PUBLICATIONS

Joucla, G. et al, J Chromatography B, (2013) vols. 942-943; pp. 126-133.
Mihara, et al., Journal of Pharmaceutical Sciences, (2015) 104:3991-3996.
Valente, K., et al, Biotechnology and Bioengineering, 112: 12302-1242 doi:10.1002/bit.25515 (First published online Jan. 16, 2015).
Kishore, R.K. et al., "The Degradation of Polysorbates 20 and 80 and Its potential Impact on the Stability of Biotherapeutics," Phar. Res. 28: 1194-1210 (2011).
"GE Healthcare Life Sciences Hydrophobic Interaction Chromatography (HIC) Selection Guide," Jun. 2012, retrieved on Mar. 7, 2016 from http://www.gelifesciences.com/gehcls_images/GELS/Related%20Content/Files/1349939730181/litdoc29022223_20130925000229.pdf.
International Search Report & Written Opinion of the International Searching Authority for International application No. PCT/US2015,054600, dated Dec. 16, 2015.
Akoh et al., "GDSL family of serine esterases/lipases" Progress in Lipid Research 43 (2004) 534-552.
Gassama—Dauge, et al. "Substrate Specificity of Phospholipase B from Guinea Pig Intestine-A glycerol ester lipase with broad specificity," J. Biol. Chem. Issue of Jul. 5, 1992, 267(19), pp. 13418-13424.
Hogwood et al., "Measurement and control of host cell proteins (HCPs) in CHO cell bioprocesses," Curr. Opin. Biotechnol. 30:153-160 (2014).
Jensen et al., "Biochemical characterization and liposomal localization localization of the mannose-6-phosphate protein p76," Biochem. J. 402: 449-458 (2007).
Kishore, R. K., Degradation of Polysorbates 20 and 80: Studies on Thermal Autoxidation and Hydrolysis:, J. Pharmacol. Sci., 100(2):721-31 (2011) Published online Aug. 27, 2010 in Wiley Online Library.

(Continued)

*Primary Examiner* — Yunsoo Kim
(74) *Attorney, Agent, or Firm* — Bookoff McAndrews, PLLC

(57) ABSTRACT

The present disclosure provides a stable protein composition containing a surfactant and having less than 400 subvisible particles of 10 microns or greater diameter per container, or less than 10,000 subvisible particles of 2 microns or greater per container. A method of manufacturing such a stable protein composition is disclosed, which includes a unit of operation that removes or decreases an esterase activity that degrades the surfactant. The unit of operation may be hydrophobic interaction chromatography or filtration, mixed mode chromatography, or the like.

Figure 1:
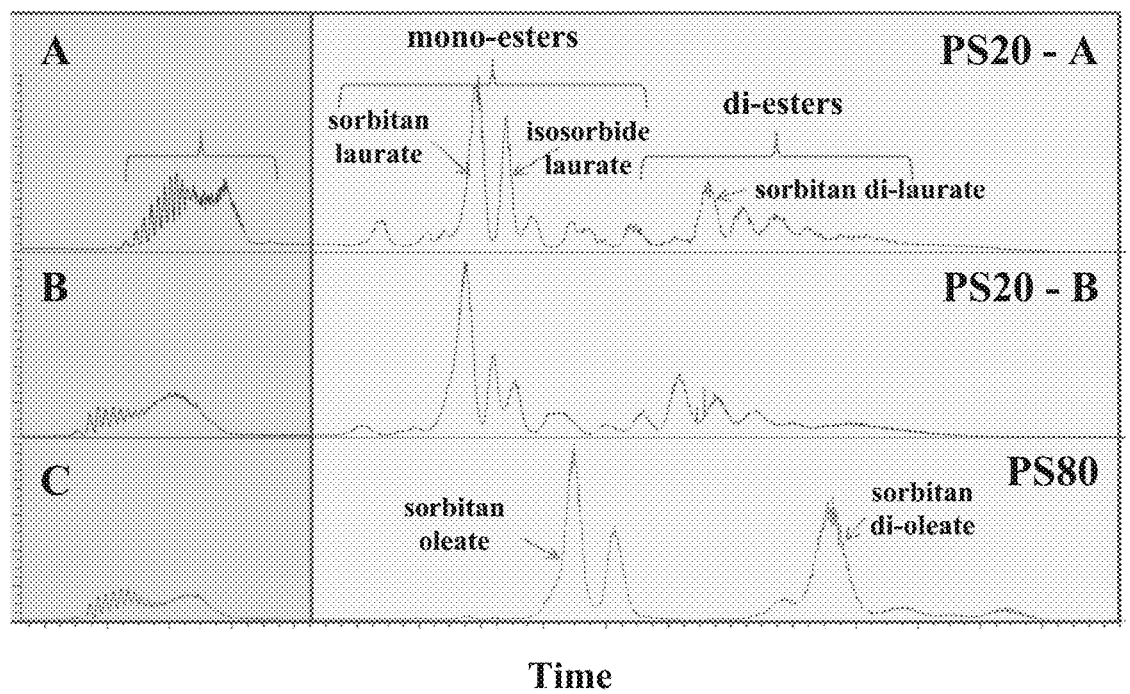

21 Claims, 2 Drawing Sheets
Specification includes a Sequence Listing.

(56) References Cited

OTHER PUBLICATIONS

Kuczewski et al., "Development of a polishing step using a hydrophobic interaction membrane adsorber with a PER. C6®-derived recombinant antibody," Biotech. Bioeng. 105(2):296-305 (2010).
Labrenz, S.R., "Ester hydrolysis of polysorbate 80 in mAb drug product: evidence in support of the hypothesized risk after observation of visible particulate in mAb formulations," J. Pharma. Sci. 103(8):2268-77 (2014).
Li et al., "Characterization and stability study of polysorbate 20 in therapeutic monoclonal antibody formulation by multidimensional ultrahigh-performance liquid chromatography-charged aerosol detection-mass spectrometry," Anal Chem. May 20, 2014;86(10):5150-7.
Morgan et al., "Identification of phospholipase B from Dictyostelium discoideum reveals a new lipase family present in mammals, flies and nematodes, but not yeast," Biochem. J. 382: 441-449 (2004).
Müller and Franzreb, "Suitability of commercial hydrophobic interaction sorbents for temperature controlled protein liquid chromatography under low salt conditions," J. Chroma. A 1260:88-96 (2012).
Narhi et al., "A critical review of analytical methods for subvisible and visible particles," Curr Pharm Biotechnol 10 (4):373-381 (2009).
Repo, H., et al. "Is the bovine lysosomal phospholipase B-like protein an amidase?" Proteins, 82:300-311 (2014), Published online Aug. 12, 2013 in Wiley Online Library.
Roettger and Ladisch, "Hydrophobic interaction chromatography," Biotechnol Adv. 7(1):15-29 (1989).
Saggu et al., "Identification of Subvisible Particles in Biopharmaceutical Formulations Using Raman Spectroscopy Provides Insight into Polysorbate 20 Degradation Pathway," Pharm Res. Sep. 2015;32(9):2877-88.
Sharma et al., "Micro-flow imaging: Flow microscopy applied to sub-visible particulate analysis in protein formulations," AAPS J. 12(3): 455-464 (2010).
Shukla and Sanchayita, "Process for purifying proteins in a hydrophobic interaction chromatography flow-through traction," U.S. Pat. No. 7,427,659 B2, dated Sep. 23, 2008.
Singh et al., "An industry perspective on the monitoring of subvisible particles as a quality attribute for protein therapeutics," J. Pharma. Sci. 99(8):3302-21 (2010).
Singh and Toler, "Monitoring of subvisible particles in therapeutic proteins," Methods Mol Biol. (2012); 899:379-401.
Singh, N. et al, Clarification of Recombinant Proteins From High Cell Density Mammalian Cell Culture Systems Using New Improved Depth Filters Biotechnol. Bioeng., vol. 110(7):1964-1972 (2013).
Siska et al., "Free fatty acid particles in protein formulations, part 2: Contribution of polysorbate raw material," J. Pharma. Sci. 104(2):447-56 (Epub Sep. 5, 2014).
Tait, A. S., et al. "Differential Response in Downstream Processing of CHO Cells Grown Under Mild Hypothermic Conditions" Chemical Engineers Biotechnol. Prog., 29:688-696 (2013).
Wilton, David C. and Waite, Moseley, Chapter 11: Phospholipases. D.E. Vance and J.E. Vance (Eds.) Biochemistry Lipids, Lipoproteins and Membranes (4th Edn.), pp. 291-314 (2002).
Vanderlaan, M., "Recent experiences with Host Cell Protein Impurity Analysis," CaSSS Conference (proceedings), Nov. 13, 2014.
Vanderlaan et al., "Hamster Phospholipase B-Like 2 (PLBL2): A Host-Cell Protein Impurity in Therapeutic Monoclonal Antibodies Derived from Chinese Hamster Ovary Cells," Bioprocess International 2015.
Yuk, et al., "More similar than different: Host cell protein production using three null CHO cell lines," Biotechnol Bioeng. Oct. 2015;112(10):2068-83.
Zhang Q, et al. "Comprehensive tracking of host cell proteins during monoclonal antibody purifications using mass spectrometry" mAbs 6(3):659-670; (May/Jun. 2014).
Hanania et al. "Lebrikizumab in moderate-to-severe asthma: pooled data from two randomized placebo-controlled studies" downloaded from http://thorax.bmj.com/ on Jul. 14, 2017,—published by group.bmj.com (10 pages).
Daniel Song, Ph.D. "ChP Monograph: Polysorbate 80 (PS 80) for Injectable Product" PS 80 Workshop with Chinese Pharmacopeia Commission (CPC) Apr. 26, 2017, (12 pages).
Carpenter et al. "Overlooking Subvisible Particles in Therapeutic Protein Products: Gapes That May Compromise Product Quality" published online Aug. 14, 2008 in Wiley InterScience (www.interscience.wiley.com). DOI 10.1002/jps.21530 (5 pages).
Doshi et al. "Understanding Particle Formation: Solubility of Free Fatty Acids as Polysorbate 20 Degradation Byproducts in Therapeutic Monoclonal Antibody Formulations" 2015 American Chemical Society DOI: 10.1021/acs.molpharmaceut.5b00310 Mol. Pharmaceutics 2015, 12, 3792-3804 (13 pages).
Narhi et al. "Subvisible (1-100 um) Particle Analysis During Biotherapeutic Drug Product Development: Part 1, Considerations and Strategy" published online Apr. 1, 2015 in Wiley Online Library (wileyonlinelibrary.com). DOI 10.1002/jps.24437 Journal of Pharaceutical Sciences pp. 1899-1908 (10 pages).

\* cited by examiner

PROCESS FOR REDUCING SUBVISIBLE PARTICLES IN A PHARMACEUTICAL FORMULATION

CROSS-REFERENCE TO RELATED APPLICATIONS

This application claims priority to U.S. Provisional Application No. 62/061,797 filed Oct. 9, 2014, the disclosure of which is incorporated herein by reference.

FIELD

This disclosure is directed to stable biopharmaceutical formulation compositions that do not form meaningful amounts of subvisible particles over time, and to methods of making the stable biopharmaceutical formulations that do not form meaningful amounts of subvisible particles over time. This disclosure is also directed to compositions and methods of making biopharmaceutical formulations containing an intact emulsifier or stabilizer containing a fatty acid ester moiety.

BACKGROUND

Biopharmaceutical drugs (or biologics) often contain proteins or nucleic acid molecules. These molecules are quite often fairly large and prone to long term instability. In order to maintain efficacy over time, reduce immunogenicity and inflammatory reactions, and to meet regulatory requirements, these biologics must exhibit long term stability and a commercially reasonable shelf life.

Biological formulations may be subject to the formation of particulate matter over time during storage. Particles may be visible or subvisible. Subvisible particles are generally under 150 microns or 100 microns in diameter. Some particles may be "foreign", that is a contaminant apart from the biological molecule. However, in those biological formulations containing proteins, the proteins may self-aggregate to form particles. Excessive handling, agitation, thermal stress, freeze-thaw, the introduction of trace nanoparticles such as silicone oils and other substances associated with vials and syringe barrels may contribute to protein aggregation and the formation of subvisible particles. Formulations having high protein concentrations, e.g., more concentrated than about 30 mg/mL, are more prone to aggregation and subvisible particle formation.

Given the potential risks associated with the inclusion of subvisible particles, regulatory authorities like the FDA provide limitations on the number of subvisible particles allowed in a pharmaceutical formulation. For example, USP 31 monograph <788> sets the limit for number of particles allowed in parenteral formulations. For large volume parenterals (greater than 100 mL), the limit is set at no more than 25 particles of at least 10 microns per mL, and no more than 3 particles of at least 25 microns per mL. For small volume parenterals (100 mL or less), the limit is set at no more than 6,000 particles of at least 10 microns per container, and no more than 600 particles of at least 25 microns per container.

To prevent or reduce the rate of particle formation in proteinaceous formulations, formulators of ordinary skill add stabilizers to the formulations. Those stabilizers include surface active agents and organic co-solvents such as polysorbates surfactants and copolymers. Copolymers include for example ethylene oxide/polypropylene oxide copolymers. Polysorbates generally used in pharmaceutical preparations include polysorbate 20 and polysorbate 80, but others may be used as well.

Polysorbates are fatty acid esters of PEG-ylated sorbitan (polyoxyethylene sorbitan esters). The polyoxyethylene serves as the hydrophilic head group and the fatty acid as the lipophilic tail. The effectiveness as a surfactant of the polysorbate depends upon both groups being present in a single molecule. When a polysorbate degrades (hydrolyzes) into its component head group and fatty acid tail, it loses its effectiveness as a protein stabilizer, potentially allowing for aggregation and subsequent subvisible particle formation. Therefore, in biopharmaceutical formulations that employ polysorbates as protein stabilizers, the stability of the polysorbates themselves is important for proper function and prevention of the formation of subvisible particles.

SUMMARY

The applicants have made the surprising discovery that an esterase, present as a host cell protein, may be co-purified with a protein of interest; and that the esterase may degrade the surfactant present in a formulation containing the protein of interest in some instances leading to loss of surfactant activity and the formation of protein aggregates and subvisible particles.

Thus, in one aspect the invention provides a composition comprising a protein, a fatty acid ester surfactant, and less than 400 subvisible particles per container, wherein the subvisible particles have a diameter that is 10 microns or greater. In one embodiment, the composition comprises less than 10,000 subvisible particles, wherein the subvisible particles have a diameter of at least 2 microns or more. In some embodiments, the subvisible particles have a diameter of greater than or equal to ten microns. In others, the diameter of the subvisible particles is greater than or equal to 500 nanometers. In still other embodiments, the diameter of the subvisible particles is greater than or equal to 25 microns. In some embodiments, the subvisible particles have a diameter that is less than 150 microns or less than 100 microns. In other embodiments, the subvisible particles are greater than or equal to 2 microns in diameter.

In one embodiment, the protein is an antibody. In some cases the concentration of the antibody is high, for example at least 30 mg/mL, at least 40 mg/mL, at least 80 mg/mL, or at least 100 mg/mL.

In one embodiment, the fatty acid ester comprises one or more fatty acids with an aliphatic tail of about 6 carbons to 21 carbons. In some cases the aliphatic tail has at least 18 carbons, such as oleate, linoleate, arachidonate, and the like. In other cases the aliphatic tail has less than 18 carbons, such as laurate, caprate, caprylate, myristate, palmitate, palmitoleate, and the like. The fatty acid can be saturated, or unsaturated to various degrees. In some embodiments, the fatty acid ester is a detergent, such as an ionic, polar, or non-ionic detergent.

In some embodiments, the fatty acid ester is a polyoxyethylene sorbitan fatty acid ester. In one embodiment, the fatty acid ester is polyoxyethylene (20) sorbitan oleate. In another embodiment, the fatty acid ester is polyoxyethylene (20) sorbitan laurate.

In some embodiments, the composition has reduced levels of esterase activity such that the fatty acid ester in the composition remains essentially intact. In some embodiments, the composition is free of detectable esterase activity. The esterase may be a carboxylic ester hydrolase (EC 3.1.1), such as for example a lipase. In one embodiment, the esterase is a phospholipase B-like 2 esterase, such as a *Cricetulus* sp. phospholipase B-like 2 esterase. In a specific embodiment, the esterase comprises an amino acid sequence of SEQ ID NO:1.

In some embodiments, the composition comprises a buffer and/or a thermal stabilizer.

In some embodiments, the composition is or was stored for some time at some temperature. In one embodiment, the composition was stored for at least six months at 5° C.

In a second aspect, the invention provides a composition that contains a protein and an intact fatty acid ester. What is meant by intact is that the fatty acid ester is essentially undegraded such that less than 20% by mole of the fatty acid ester is hydrolyzed into a free fatty acid and head group. In other words, in a composition in which 20% of a fatty acid ester having a single fatty acid chain has hydrolyzed, there are 4 moles of fatty acid ester per mole of free fatty acid. For fatty acid esters with two fatty acid chains, 20% hydrolyzed converts to 4 moles of fatty acid ester per two moles of free fatty acid. For fatty acid esters with three fatty acid chains, 20% hydrolyzed converts to 4 moles of fatty acid ester per three moles of free fatty acid.

In one embodiment, no more than 15% of the fatty acid ester is hydrolyzed into the free fatty acid and head group (≥17 moles of monoester per 3 moles of free fatty acid), no more than 10% of the fatty acid ester is hydrolyzed into the free fatty acid and head group (≥9 moles of monoester per mole of free fatty acid), or no more than 5% of the fatty acid ester is hydrolyzed into the free fatty acid and head group (≥19 moles of monoester per mole of free fatty acid).

In one embodiment, the protein is an antibody. In some cases the concentration of the antibody is high, for example at least 30 mg/mL, at least 40 mg/mL, at least 80 mg/mL, or at least 100 mg/mL.

In one embodiment, the fatty acid ester comprises one or more fatty acids with an aliphatic tail of from about 6 carbons to 21 carbons. In some cases the aliphatic tail has at least 18 carbons, such as oleate, linoleate, arachidonate, and the like. In other cases the aliphatic tail has less than 18 carbons, such as laurate, caprate, caprylate, myristate, palmitate, palmitoleate, and the like. The fatty acid can be saturated, or unsaturated to various degrees. In some embodiments, the fatty acid ester is a detergent, such as an ionic, a polar, or a non-ionic detergent.

In some embodiments, the fatty acid ester is a polyoxyethylene sorbitan fatty acid ester. In one embodiment, the fatty acid ester is polyoxyethylene (20) sorbitan oleate. In another embodiment, the fatty acid ester is polyoxyethylene (20) sorbitan laurate.

In some embodiments, the composition has reduced levels of esterase activity such that the fatty acid ester in the composition remains essentially intact. In some embodiments, the composition is free of detectable esterase activity. The esterase may be a carboxylic ester hydrolase (EC 3.1.1), such as for example a lipase. In one embodiment, the esterase is a phospholipase B-like 2 esterase, such as a *Cricetulus* sp. phospholipase B-like 2 esterase. In a specific embodiment, the esterase comprises an amino acid sequence of SEQ ID NO:1.

In some embodiments, the composition comprises a buffer and/or a thermal stabilizer.

In some embodiments, the composition is or was stored for some time at some temperature. In one embodiment, the composition was stored for at least six months at 5° C.

In a third aspect, the invention provides a process for manufacturing a stable protein formulation comprising the steps of (a) contacting a hydrophobic interaction media with a composition comprising a protein of interest and an esterase; and (b) collecting the protein of interest from the media. The protein of interest collected from the media (either as flow through in the loading or wash solution, or as elution in a wash or elution solution) is associated with a reduced amount of esterase. In some cases, no esterase activity is detected in the collection containing the protein of interest.

In one embodiment, the protein of interest is an antibody, such as a monoclonal antibody, a bispecific antibody, and/or inter alia a therapeutic antibody, or fragments thereof.

In one embodiment, the esterase is a carboxylic ester hydrolase (EC 3.1.1), such as for example a lipase. In one embodiment, the esterase is capable of hydrolyzing a fatty acid ester of a sorbitan or iso-sorbide. In one embodiment, the esterase is a phospholipase B-like 2 esterase, such as a *Cricetulus* sp. phospholipase B-like 2 esterase or other rodent phospholipase B-like 2 esterase. In a specific embodiment, the esterase comprises an amino acid sequence of SEQ ID NO:1.

In some embodiments, the collected protein of interest is further processed. In some cases, the collected protein of interest is subjected to a buffer exchange, filtration, and/or additional chromatographic steps. In one embodiment, the protein of interest is concentrated at some point after collection.

In one embodiment, the collected protein of interest is combined at some point with a fatty acid ester that serves as a surfactant to prevent protein aggregation and/or subvisible particle formation. In some cases, the fatty acid ester is a polyoxyethylene (20) sorbitan ester, such as polyoxyethylene (20) sorbitan monolaurate or polyoxyethylene (20) sorbitan monooleate.

In one embodiment, the protein of interest plus fatty acid ester combination is combined with a buffer and a thermal stabilizer.

In a fourth aspect, the invention provides a process for reducing esterase activity in a composition that contains a protein of interest, the process comprising the steps of (a) contacting a composition, which contains a protein of interest and an esterase, to a medium; (b) separating the protein of interest from the esterase; and (c) collecting the protein of interest. A "medium" can be any format, such as for example a chromatography resin, beads, cellulosic substrate, a membrane, or the like. In some embodiments the medium is a hydrophobic interaction medium, which can be a hydrophobic interaction chromatography (HIC) resin or an HIC membrane. In other embodiments, the medium is a fatty acid affinity medium, which contains a ligand or adduct linked to a substrate, such that the ligand or adduct binds to a fatty acid or aliphatic tail thereof.

In one embodiment, the protein of interest is an antibody, such as a monoclonal antibody, a bispecific antibody, and/or inter alia a therapeutic antibody, or fragments thereof.

In one embodiment, the esterase is a carboxylic ester hydrolase (EC 3.1.1), such as for example a lipase. In one embodiment, the esterase is capable of hydrolyzing a fatty acid ester of a sorbitan or iso-sorbide. In one embodiment, the esterase is a phospholipase B-like 2 esterase, such as a *Cricetulus* sp. phospholipase B-like 2 esterase or other rodent phospholipase B-like 2 esterase. In a specific embodiment, the esterase comprises an amino acid sequence of SEQ ID NO: 1.

In some embodiments, the collected protein of interest is further processed. In some cases, the collected protein of interest is subjected to a buffer exchange, filtration, and/or additional chromatographic steps. In one embodiment, the protein of interest is concentrated at some point after collection.

In one embodiment, the collected protein of interest is combined at some point with a fatty acid ester that serves as a surfactant to prevent protein aggregation and/or subvisible particle formation. In some cases, the fatty acid ester is a polyoxyethylene (20) sorbitan ester, such as polyoxyethylene (20) sorbitan monolaurate or polyoxyethylene (20) sorbitan monooleate.

In one embodiment, the protein of interest plus fatty acid ester combination is combined with a buffer and a thermal stabilizer.

In a fifth aspect, the invention provides a process for reducing the formation of subvisible particles in a composition that contains a protein of interest. The process comprises the steps of (a) removing esterase activity from the composition and (b) adding a fatty acid ester to the composition. In one embodiment, less than 400 particles having an average mean diameter of 10 microns or more form in a container containing the composition after storage for six months at 5° C. In another embodiment, less than 10,000 particles having an average mean diameter of 2 microns or more form in a container containing the composition after storage for six months at 5° C.

In one embodiment, the esterase is removed from the composition by contacting the composition to a medium. The "medium" can be any format, such as chromatography resin, beads, a cellulosic substrate, a membrane, or the like. In some embodiments the medium is a hydrophobic interaction medium, which can be a hydrophobic interaction chromatography (HIC) resin or an HIC membrane. In other embodiments, the medium is a fatty acid affinity medium, which contains a ligand or adduct linked to a substrate, wherein the ligand or adduct binds to a fatty acid or aliphatic tail thereof.

In one embodiment, the protein of interest is an antibody, such as a monoclonal antibody, a bispecific antibody, and/or inter alia a therapeutic antibody, or fragments thereof.

In one embodiment, the esterase is a carboxylic ester hydrolase (EC 3.1.1), such as for example a lipase. In one embodiment, the esterase is capable of hydrolyzing a fatty acid ester of a sorbitan or an iso-sorbide. In a specific embodiment, the esterase preferentially hydrolyzes polyoxyethylene (20) sorbitan monolaurate over polyoxyethylene (20) sorbitan monooleate. In one embodiment, the esterase is a phospholipase B-like 2 esterase, such as a *Cricetulus* sp. phospholipase B-like 2 esterase or other rodent phospholipase B-like 2 esterase. In a specific embodiment, the esterase comprises an amino acid sequence of SEQ ID NO:1.

In some embodiments, the collected protein of interest is further processed. In some cases, the collected protein of interest is subjected to a buffer exchange, filtration, and/or additional chromatographic steps. In one embodiment, the protein of interest is concentrated at some point after collection.

In one embodiment, the collected protein of interest is combined at some point with a fatty acid ester that serves as a surfactant or emulsifier to prevent protein aggregation and/or subvisible particle formation. In some cases, the fatty acid ester is a polyoxyethylene (20) sorbitan ester, such as polyoxyethylene (20) sorbitan monolaurate or polyoxyethylene (20) sorbitan monooleate.

In one embodiment, the protein of interest plus fatty acid ester combination is combined with a buffer and a thermal stabilizer.

In one embodiment, the composition is stored at 5° C. for at least 6 months.

DRAWINGS

FIG. 1 depicts a chromatogram showing relative amounts of different molecular species within (A) lower quality polysorbate 20 (PS20-A), (B) higher quality polysorbate 20 (PS20-B), and (C) polysorbate 80 (PS80).

Figure 2:
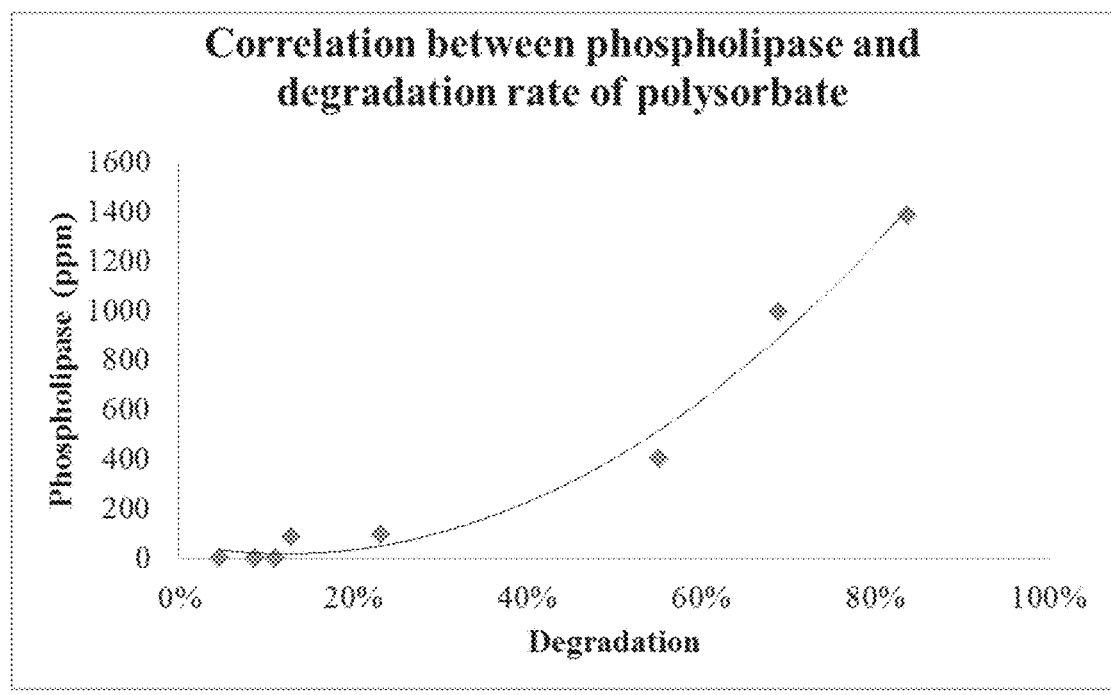

FIG. 2 depicts a graph showing the correlation between phospholipase activity (in parts per million) and percent degradation of polysorbate 20.

DETAILED DESCRIPTION

This invention is not limited to particular methods and experimental conditions described, as such methods and conditions may vary. It is also to be understood that the terminology used herein is for the purpose of describing particular embodiments only, and is not intended to be limiting, since the scope of the present invention is defined by the claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, particular methods and materials are now described. All publications mentioned are hereby incorporated by reference.

Definitions

The term "protein" means any amino acid polymer having more than about 20 amino acids covalently linked via amide bonds. Proteins contain one or more amino acid polymer chains, generally known in the art as "polypeptides". Thus, a polypeptide may be a protein, and a protein may contain multiple polypeptides to form a single functioning biomolecule of a single conformation. Disulfide bridges (between cysteine residues to form cystine) may be present in some proteins. These covalent links may be within a single polypeptide chain, or between two individual polypeptide chains. For example, disulfide bridges are essential to proper structure and function of insulin, immunoglobulins, protamine, and the like. For a recent review of disulfide bond formation, see Oka and Bulleid, "Forming disulfides in the endoplasmic reticulum," *Biochim Biophys Acta,* 2013 November; 1833(11):2425-9.

In addition to disulfide bond formation, proteins may be subject to other post-translational modifications. Those modifications include lipidation (e.g., myristoylation, palmitoylation, farnesoylation, geranylgeranylation, and glycosylphosphatidylinositol (GPI) anchor formation), alkylation (e.g., methylation), acylation, amidation, glycosylation (e.g., addition of glycosyl groups at arginine, asparagine, cysteine, hydroxylysine, serine, threonine, tyrosine, and/or tryptophan), and phosphorylation (i.e., the addition of a phosphate group to serine, threonine, tyrosine, and/or histidine). For a recent review on the post-translational modification of proteins produced in eukaryotes, see Mowen and David, "Unconventional post-translational modifications in immunological signaling," Nat Immunol, 2014 June; 15(6):512-20; and Blixt and Westerlind, "Arraying the post-translational glycoproteome (PTG)," *Curr Opin Chem Biol,* 2014 February; 18:62-9.

Immunoglobulins are proteins having multiple polypeptide chains and extensive post-translational modifications. The canonical immunoglobulin protein (e.g., IgG) comprises four polypeptide chains—two light chains and two heavy chains. Each light chain is linked to one heavy chain via a cystine disulfide bond, and the two heavy chains are bound to each other via two cystine disulfide bonds. Immunoglobulins produced in mammalian systems are also glycosylated at various residues (e.g., at asparagine residues) with various polysaccharides, and can differ from species to species, which may affect antigenicity for therapeutic antibodies (see Butler and Spearman, "The choice of mammalian cell host and possibilities for glycosylation engineering", Curr Opin Biotech, 2014 December.; 30:107-112).

As used herein, "protein" includes biotherapeutic proteins, recombinant proteins used in research or therapy, trap proteins and other Fc-fusion proteins, chimeric proteins, antibodies, monoclonal antibodies, human antibodies, bispecific antibodies, antibody fragments, nanobodies, recombinant antibody chimeras, cytokines, chemokines, peptide hormones, and the like. Proteins may be produced using recombinant cell-based production systems, such as the insect bacculovirus system, yeast systems (e.g., *Pichia* sp.), mammalian systems (e.g., CHO cells and CHO derivatives like CHO-K1 cells). For a recent review discussing biotherapeutic proteins and their production, see Ghaderi et al., "Production platforms for biotherapeutic glycoproteins. Occurrence, impact, and challenges of non-human sialylation," *Biotechnol Genet Eng Rev.* 2012; 28:147-75.

The term "antibody", as used herein, includes immunoglobulin molecules comprised of four polypeptide chains, two heavy (H) chains and two light (L) chains inter-connected by disulfide bonds. Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3. The term "high affinity" antibody refers to those antibodies having a binding affinity to their target of at least 10-9 M, at least 10-1 M; at least 10-11 M; or at least 10-12 M, as measured by surface plasmon resonance, e.g., BIACORE™ or solution-affinity ELISA.

The phrase "bispecific antibody" includes an antibody capable of selectively binding two or more epitopes. Bispecific antibodies generally comprise two different heavy chains, with each heavy chain specifically binding a different epitope—either on two different molecules (e.g., antigens) or on the same molecule (e.g., on the same antigen). If a bispecific antibody is capable of selectively binding two different epitopes (a first epitope and a second epitope), the affinity of the first heavy chain for the first epitope will generally be at least one to two or three or four orders of magnitude lower than the affinity of the first heavy chain for the second epitope, and vice versa. The epitopes recognized by the bispecific antibody can be on the same or a different target (e.g., on the same or a different protein). Bispecific antibodies can be made, for example, by combining heavy chains that recognize different epitopes of the same antigen. For example, nucleic acid sequences encoding heavy chain variable sequences that recognize different epitopes of the same antigen can be fused to nucleic acid sequences encoding different heavy chain constant regions, and such sequences can be expressed in a cell that expresses an immunoglobulin light chain. A typical bispecific antibody has two heavy chains each having three heavy chain CDRs, followed by (N-terminal to C-terminal) a CH1 domain, a hinge, a CH2 domain, and a CH3 domain, and an immunoglobulin light chain that either does not confer antigen-binding specificity but that can associate with each heavy chain, or that can associate with each heavy chain and that can bind one or more of the epitopes bound by the heavy chain antigen-binding regions, or that can associate with each heavy chain and enable binding or one or both of the heavy chains to one or both epitopes.

The phrase "heavy chain," or "immunoglobulin heavy chain" includes an immunoglobulin heavy chain constant region sequence from any organism, and unless otherwise specified includes a heavy chain variable domain. Heavy chain variable domains include three heavy chain CDRs and four FR regions, unless otherwise specified. Fragments of heavy chains include CDRs, CDRs and FRs, and combinations thereof. A typical heavy chain has, following the variable domain (from N-terminal to C-terminal), a CH1 domain, a hinge, a CH2 domain, and a CH3 domain. A functional fragment of a heavy chain includes a fragment that is capable of specifically recognizing an antigen (e.g., recognizing the antigen with a KD in the micromolar, nanomolar, or picomolar range), that is capable of expressing and secreting from a cell, and that comprises at least one CDR.

The phrase "light chain" includes an immunoglobulin light chain constant region sequence from any organism, and unless otherwise specified includes human kappa and lambda light chains. Light chain variable (VL) domains typically include three light chain CDRs and four framework (FR) regions, unless otherwise specified. Generally, a full-length light chain includes, from amino terminus to carboxyl terminus, a VL domain that includes FR1-CDR1-FR2-CDR2-FR3-CDR3-FR4, and a light chain constant domain. Light chains that can be used with this invention include those, e.g., that do not selectively bind either the first or second antigen selectively bound by the antigen-binding protein. Suitable light chains include those that can be identified by screening for the most commonly employed light chains in existing antibody libraries (wet libraries or in silico), where the light chains do not substantially interfere with the affinity and/or selectivity of the antigen-binding domains of the antigen-binding proteins. Suitable light chains include those that can bind one or both epitopes that are bound by the antigen-binding regions of the antigen-binding protein.

The phrase "variable domain" includes an amino acid sequence of an immunoglobulin light or heavy chain (modified as desired) that comprises the following amino acid regions, in sequence from N-terminal to C-terminal (unless otherwise indicated): FR1, CDR1, FR2, CDR2, FR3, CDR3, FR4. A "variable domain" includes an amino acid sequence capable of folding into a canonical domain (VH or VL) having a dual beta sheet structure wherein the beta sheets are connected by a disulfide bond between a residue of a first beta sheet and a second beta sheet.

The phrase "complementarity determining region," or the term "CDR," includes an amino acid sequence encoded by a nucleic acid sequence of an organism's immunoglobulin genes that normally (i.e., in a wild-type animal) appears between two framework regions in a variable region of a light or a heavy chain of an immunoglobulin molecule (e.g., an antibody or a T cell receptor). A CDR can be encoded by, for example, a germline sequence or a rearranged or unrearranged sequence, and, for example, by a naive or a mature B cell or a T cell. In some circumstances (e.g., for a CDR3), CDRs can be encoded by two or more sequences (e.g., germline sequences) that are not contiguous (e.g., in an unrearranged nucleic acid sequence) but are contiguous in a B cell nucleic acid sequence, e.g., as the result of splicing or connecting the sequences (e.g., V-D-J recombination to form a heavy chain CDR3).

The phrase "Fc-containing protein" includes antibodies, bispecific antibodies, immunoadhesins, and other binding proteins that comprise at least a functional portion of an immunoglobulin CH2 and CH3 region. A "functional portion" refers to a CH2 and CH3 region that can bind a Fc receptor (e.g., an FcγR; or an FcRn, i.e., a neonatal Fc receptor), and/or that can participate in the activation of complement. If the CH2 and CH3 region contains deletions, substitutions, and/or insertions or other modifications that render it unable to bind any Fc receptor and also unable to activate complement, the CH2 and CH3 region is not functional.

Fc-containing proteins can comprise modifications in immunoglobulin domains, including where the modifications affect one or more effector function of the binding protein (e.g., modifications that affect FcγR binding, FcRn binding and thus half-life, and/or CDC activity). Such modifications include, but are not limited to, the following modifications and combinations thereof, with reference to EU numbering of an immunoglobulin constant region: 238, 239, 248, 249, 250, 252, 254, 255, 256, 258, 265, 267, 268, 269, 270, 272, 276, 278, 280, 283, 285, 286, 289, 290, 292, 293, 294, 295, 296, 297, 298, 301, 303, 305, 307, 308, 309, 311, 312, 315, 318, 320, 322, 324, 326, 327, 328, 329, 330, 331, 332, 333, 334, 335, 337, 338, 339, 340, 342, 344, 356, 358, 359, 360, 361, 362, 373, 375, 376, 378, 380, 382, 383, 384, 386, 388, 389, 398, 414, 416, 419, 428, 430, 433, 434, 435, 437, 438, and 439.

For example, and not by way of limitation, the binding protein is an Fc-containing protein and exhibits enhanced serum half-life (as compared with the same Fc-containing protein without the recited modification(s)) and have a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at 428 and/or 433 (e.g., L/R/SI/P/Q or K) and/or 434 (e.g., H/F or Y); or a modification at 250 and/or 428; or a modification at 307 or 308 (e.g., 308F, V308F), and 434. In another example, the modification can comprise a 428L (e.g., M428L) and 434S (e.g., N434S) modification; a 428L, 259I (e.g., V259I), and a 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); a 307 and/or 308 modification (e.g., 308F or 308P).

The term "cell" includes any cell that is suitable for expressing a recombinant nucleic acid sequence. Cells include those of prokaryotes and eukaryotes (single-cell or multiple-cell), bacterial cells (e.g., strains of E. coli, Bacillus spp., Streptomyces spp., etc.), mycobacteria cells, fungal cells, yeast cells (e.g., S. cerevisiae, S. pombe, P. pastoris, P. methanolica, etc.), plant cells, insect cells (e.g., SF-9, SF-21, baculovirus-infected insect cells, Trichoplusia ni, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g. a retinal cell that expresses a viral gene (e.g., a PER.C6™ cell).

The term "fatty acid ester" means any organic compound that contains a fatty acid chain linked to a head group via an ester bond. An ester bond is formed when a hydroxyl group (e.g., an alcohol or carboxylic acid) is replaced by an alkoxy group. As used herein, the hydroxyl group can be part of a carboxylic acid, more specifically a fatty acid, and/or an alcohol, such as glycerol, sorbitol, sorbitan, isosorbide, or the like. The alcohol group is generally referred to herein as the head group.

Examples of fatty acid esters generally include phospholipids, lipids (e.g., the head group is glycerol, including monoglycerides, diglycerides, and triglycerides), and surfactants and emulsifiers, including for example polysorbates like polysorbate 20, polysorbate 60, and polysorbate 80, which are non-ionic detergents. Surfactants and emulsifiers are useful as cosolvents and stabilizers. They function by associating with both a hydrophilic surface and a lipophilic surface to maintain dispersion and structural stability of ingredients, like proteins. Surfactants are added to protein formulations primarily to enhance protein stability against mechanical stress, such as air/liquid interface and solid/liquid interface shear. Without a surfactant, proteins may in some cases become structurally unstable in solution, and form multimeric aggregates that eventually become subvisible particles.

The term "fatty acid" or "fatty acid chain" means a carboxylic acid having an aliphatic tail. An aliphatic tail is simply a hydrocarbon chain comprising carbon and hydrogen, and in some cases, oxygen, sulfur, nitrogen and/or chlorine substitutions. Aliphatic tails can be saturated (as in saturated fatty acids), which means that all carbon-carbon bonds are single bonds (i.e., alkanes). Aliphatic tails can be unsaturated (as in unsaturated fatty acids), wherein one or more carbon-carbon bonds are double bonds (alkenes), or triple bonds (alkanes).

Fatty acids are generally designated as short-chain fatty acids, which have fewer than six carbons in their aliphatic tails, medium-chain fatty acids having six to twelve carbons, long-chain fatty acids having thirteen to twenty one carbons, and very long chain fatty acids having aliphatic tails of twenty two carbons and longer. As mentioned above, fatty acids are also categorized according to their degree of saturation, which correlates to stiffness and melting point. Common fatty acids include caprylic acid (8 carbons:0 double bonds; 8:0), capric acid (10:0), lauric acid (12:0), myristic acid (14:0), myristoleic acid (14:1), palmitic acid (16:0), palmitoleic acid (16:1), sapienic acid (16:1), stearic acid (18:0), oleic acid (18:1), elaidic acid (18:1), vaccenic acid (18:1), linoleic acid (18:2), linelaedic acid (18:2), alpha-linolenic acid (18:3), arachidic acid (20:0), arachidonic acid (20:4), eicosapentaenoic acid (20:5), behenic acid (22:0), erucic acid (22:1), docosahexaenoic acid (22:6), lignoceric acid (24:0), and cerotic acid (26:0).

As mentioned above, polysorbates are fatty acid esters useful as non-ionic surfactants and protein stabilizers. Polysorbate 20, polysorbate 40, polysorbate 60, and polysorbate 80 are widely employed in the pharmaceutical, cosmetic, and food industries as stabilizers and emulsifiers. Polysorbate 20 mostly comprises the monolaurate ester of polyoxyethylene (20) sorbitan. Polysorbate 40 mostly comprises the monopalmitate ester of polyoxyethylene (20) sorbitan. Polysorbate 60 mostly comprises the monostearate ester of polyoxyethylene (20) sorbitan. Polysorbate 80 mostly comprises the monooleate ester of polyoxyethylene (20) sorbitan.

The quality of commercial grades of polysorbates varies from vendor to vendor. Polysorbates therefore are often mixtures of various chemical entities, consisting mostly of polyoxyethylene (20) sorbitan monoesters (as described above) with, in some cases, isosorbide ester contaminants. The head group (in this case polyoxyethylene (20) sorbitan) comprises a sorbitan (a mixture of dehydrated sorbitols, including 1,4-anhydrosorbitol, 1,5-anhydrosorbitol, and 1,4, 3,6-dianhydrosorbitol) substituted at three of its alcohol groups to form ether bonds with three polyoxyethylene groups. The fourth alcohol group is substituted with a fatty acid to form a fatty acid ester.

In some commercially available batches of polysorbates, the polysorbate contains isosorbide monoesters. Isosorbide is a heterocyclic derivative of glucose, also prepared by the dehydration of sorbitol. It is a diol, i.e., having two alcohol groups that can take part in the formation of one or two ester bonds. Thus, for example, some lots of polysorbate 20 can contain significant amounts of isosorbide laurate mono- and di-esters.

In addition to head group variation, preparations of polysorbates contain variable amounts of other fatty acid esters. For example, an analysis of one particular source of polysorbate 20 revealed <10% caprylic acid, <10% capric acid, 40-60% lauric acid, 14-25% myristic acid, 7-15% palmitic acid, <11% oleic acid, <7% stearic acid, and <3% linoleic acid. An analysis of a polysorbate 80 batch revealed <5% myristic acid, <16% palmitic acid, >58% oleic acid, <6% stearic acid, and <18% linoleic acid.

Biopharmaceutical drugs are often formulated with non-ionic detergents like polysorbate 20 or polysorbate 80. These detergents help stabilize large molecules like antibodies and other proteins, and help prevent the formation of supermolecular ternary complexes or other aggregates. Aggregates can become nanoparticles or subvisible particles in the 10 to 100 micron range or 2 to 100 micron range, and interfere with drug product stability and shelf-life. Therefore, the stability of protein formulations depends in some cases upon the stability of the non-ionic detergent additive.

The phrase "subvisible particle" means a particle that is not visible, especially in a liquid. In other words, a solution or other liquid containing subvisible particles, but not visible particles, will not appear cloudy. Subvisible particles generally include those particles 100 micron or less in diameter, but in some cases include particles under 150 microns (Narhi et al., "A critical review of analytical methods for subvisible and visible particles," Curr Pharm Biotechnol 10(4):373-381 (2009)). Subvisible particles may be the result of foreign contaminants or protein aggregation. Protein aggregates can be soft and amorphous in shape and therefore may be difficult to detect using conventional light obscuration and microscopic methods (Singh and Toler, "Monitoring of subvisible particles in therapeutic proteins," Methods Mol Biol. 2012; 899:379-401). Subvisible particles may comprise inter alia silicone contaminants (oily droplets), free fatty acids (oily droplets), aggregated protein (amorphous particles), and/or protein/fatty acid complexes (amorphous particles).

Subvisible particles can be detected by any one or more of various methods. The USP standards specify light obscuration (Method 1) and optical microscopy (Method 2) protocols. Other methods include flow image analysis, Coulter counting, and submicron particle tracking methods. For light obscuration (LO), particles are counted based on the shadows they cast upon a light detector as they pass through a light beam in a flow cell. The size, shape and inverse intensity of the shadow depends upon the size, shape and difference in the refractive index of the particle relative to the solution. The lower size range for detection using LO is about 2 microns. A commonly used LO device is the HIAC instrument (Beckman Coulter, Brea, Calif.).

Light obscuration is criticized for underestimating protein aggregates and other amorphous structures. Flow image analysis, such as micro-flow imaging (MFI) (Brightwell Technologies, Ottawa, Ontario), is a more sensitive method of detecting the irregularly shaped, fragile, and transparent proteinaceous subvisible particles, and of differentiating those types of particles from silicone micro-droplets, air bubbles, and other foreign contaminants (Sharma et al., "Micro-flow imaging: Flow microscopy applied to sub-visible particulate analysis in protein formulations," AAPS J. 12(3): 455-464 (2010)). Briefly, MFI is flow microscopy in which successive bright field images are taken and analyzed in real time. Image analysis algorithms are applied to the images to discriminate air bubbles, silicone oil droplets, and proteinaceous aggregates. Volumes as low as about 250 microliters to as high as tens of milliliters can be analyzed. Depending on the system used, particles in the range of two to 300 microns, or one to 70 microns can be detected (Id).

The FDA and other government regulatory agencies have placed limits on the amount of subvisible particles allowed in parenteral drug formulations. The major articulated concern is the uncertainty surrounding potential immunogenicity and downstream negative effects in the patient receiving the drug (Singh et al., "An industry perspective on the monitoring of subvisible particles as a quality attribute for protein therapeutics," J. Pharma. Sci. 99(8):3302-21 (2010)). For small volume parenteral drugs (i.e., 25 mL or below), the pharmacopeia limits subvisible particles (SVP) of greater than or equal to 10 microns to no more than 6,000 SVPs per container, and SVPs of greater than or equal to 25 microns to no more than 600 per container. (United States Pharmacopeia and National Formulary (USP 33-NF 28), <788> Particulate Matter in Injections.) For ophthalmic drugs, the SVP limits are 50 per mL of 10 microns or greater, 5 per mL of 25 microns or greater, and 2 per mL of 50 microns or greater (Id at <789> Particulate Matter in Ophthalmic Solutions). Regulatory agencies are increasingly contemplating that manufacturers establish specifications for SVPs of 2 microns or greater (see Singh et al., "An industry perspective on the monitoring of subvisible particles as a quality attribute for protein therapeutics," J. Pharm. Sci. 99(8):3302-21 (2010)).

The term "esterase" means an enzyme that catalyzes the hydrolysis of an ester bond to create an acid and an alcohol. Esterases are a diverse category of enzymes, including acetyl esterases (e.g., acetylcholinesterase), phosphatases, nucleases, thiolesterases, lipases and other carboxyl ester hydrolases (EC 3.1. As its name implies a carboxyl ester hydrolase (a.k.a. carboxylesterase, carboxylic-ester hydrolase, and EC 3.1.1.1) uses water to hydrolyze a carboxylic ester into an alcohol and a carboxylate. A lipase is a carboxyl ester hydrolase that catalyzes the hydrolysis of lipids, including triglycerides, fats and oils into fatty acids and an alcohol head group. For example, triglycerides are hydrolyzed by lipases like pancreatic lipase to form monoacylglycerol and two fatty acid chains.

Phospholipases are lipases that hydrolyze phospholipids into fatty acids and other products. Phospholipases fall into four broad categories: phospholipase A (including phospholipase A1 and phospholipase A2), phospholipase B, and the phosphodiesterases phosphodiesterase C and phosphodiesterase D. In addition to the canonical phospholipases, phospholipase B-like enzymes, which reside at the lysosome lumen, are thought to be involved in lipid catalysis. For example, phospholipase B-like 2 (PLBL2) is postulated to have esterase activity based upon sequence homology and subcellular localization (Jensen et al., "Biochemical characterization and liposomal localization localization of the mannose-6-phosphate protein p76," Biochem. J. 402: 449-458 (2007)).

Applicants have discovered an enzymatic activity associated with the destabilization of polysorbates (including polysorbate 20 and polysorbate 80). That activity was found to be associated with an esterase, such as a polypeptide comprising the amino acid sequences of Table 1. A BLAST search of those peptide sequences revealed identity with a putative phospholipase B-like 2 (PLBL2). PLBL2 is highly conserved in hamster, rat, mice, human and bovine. The applicants envision that PLBL2, which copurifies under certain processes with some classes of proteins-of-interest manufactured in a mammalian cell line, has esterase activity responsible for the hydrolysis of polysorbate 20 and 80. Applicants envision that other esterase species, of which PLBL2 is an example, may contribute to polysorbate instability, depending upon the particular protein-of-interest and/or genetic/epigenetic background of the host cell.

Ester hydrolysis of polysorbate 80 was recently reported (see Labrenz, S. R., "Ester hydrolysis of polysorbate 80 in mAb drug product: evidence in support of the hypothesized risk after observation of visible particulate in mAb formulations," J. Pharma. Sci. 103(8):2268-77 (2014)). That paper reported the formation of visible particles in a formulation containing IgG. The author postulated that the colloidal IgG particles formed due to the enzymatic hydrolysis of oleate esters of polysorbate 80. Although no esterase was directly identified, the author speculates that a lipase or tweenase copurified with the IgG, which was responsible for degrading the polysorbate 80. Interestingly, IgGs formulated with polysorbate 20 did not form particles and the putative esterase did not hydrolyze the polysorbate 20. The author reported that the putative lipase associated with the IgG did not affect saturated C12 fatty acid (i.e., laurate) (Id at 7.)

TABLE 1

| Sequence Identifier | Amino acid Sequence | Sequence Identifier | Amino acid Sequence |
|---|---|---|---|
| SEQ ID NO: 1 | DLLVAHNTWNSYQNMLR | SEQ ID NO: 16 | LTLLQLKGLEDSYEGR |
| SEQ ID NO: 2 | LIRYNNFLHDPLSLCEACIPKP | SEQ ID NO: 17 | MSMLAASGPTWDQLPPFQ |
| SEQ ID NO: 3 | SVLLDAASGQLR | SEQ ID NO: 18 | VTSFSLAKR |
| SEQ ID NO: 4 | DQSLVEDMNSMVR | SEQ ID NO: 19 | QNLDPPVSR |
| SEQ ID NO: 5 | QFNSGTYNNQWMIVDYK | SEQ ID NO: 20 | IIKKYQLQFR |
| SEQ ID NO: 6 | QGPQEAYPLIAGNNLVFSSY | SEQ ID NO: 21 | AQIFQRDQSLVEDMNSMVR |
| SEQ ID NO: 7 | SMLHMGQPDLWTFSPISVP | SEQ ID NO: 22 | LIRYNNFLHDPLSLCEACIPKP |
| SEQ ID NO: 8 | YNNFLHDPLSLCEACIPKPNA | SEQ ID NO: 23 | SVLLDAASGQLR |
| SEQ ID NO: 9 | LALDGATWADIFK | SEQ ID NO: 24 | DQSLVEDMNSMVR |
| SEQ ID NO: 10 | LSLGSGSCSAIIK | SEQ ID NO: 25 | DLLVAHNTWNSYQNMLR |
| SEQ ID NO: 11 | YVQPQGCVLEWIR | SEQ ID NO: 26 | YNNFLHDPLSLCEACIPKPNA |
| SEQ ID NO: 12 | RMSMLAASGPTWDQLPPFQ | SEQ ID NO: 27 | RMSMLAASGPTWDQLPPFQ |
| SEQ ID NO: 13 | SFLEINLEWMQR | SEQ ID NO: 28 | SMLHMGQPDLWTFSPISVP |
| SEQ ID NO: 14 | VLTILEQIPGMVVVADADKTED | SEQ ID NO: 29 | MSMLAASGPTWDQLPPFQ |
| SEQ ID NO: 15 | VRSVLLDAASGQLR | SEQ ID NO: 30 | VRSVLLDAASGQLR |
| | | SEQ ID NO: 31 | QNLDPPVSR |

As used herein, the phrase "percent fatty ester hydrolysis" means the molar proportion of fatty acid ester that has been hydrolyzed. Since hydrolysis of a fatty acid ester results in the release of a free fatty acid, the percent fatty ester hydrolysis can be determined by measuring the free fatty acid in a sample. Therefore, percent fatty ester hydrolysis may be determined by calculating moles of free fatty acid divided by the sum of moles of fatty acid plus moles of fatty acid ester. In the case of percent hydrolysis of polysorbate 80 or polysorbate 20, that number may be determined by calculating the moles of free oleate or laurate (i.e., free fatty acid, a.k.a. FFA) and dividing by the total moles of remaining polysorbate plus moles of free fatty acid.

The term "esterase inhibitor" means any chemical entity that reduces, inhibits, or blocks the activity of an esterase. The applicants envision that the inclusion of an esterase inhibitor in a protein formulation containing a fatty acid ester surfactant may help maintain protein stability and help reduce SVP formation. Common esterases known in the art include orlistat (tetrahydrolipistatin; an inhibitor of carboxylesterase 2 and lipoprotein lipase), diethylumbelliferyl phosphate (a cholesterol esterase [lipsase A] inhibitor), URB602 ([1-1'-biphenyl]-3-tl-carbamicacid cyclohexyl ester; a monoacylglycerol lipase inhibitor), and 2-butoxyphenylboronic acid (an inhibitor of hormone-sensitive lipase). The inclusion of an esterase inhibitor during purification of a protein of interest or in the final formulation is expected to prevent or slow the hydrolysis of non-ionic detergents like polysorbate 20 and polysorbate 80, which in turn is expected to prevent or reduce subvisible particle formation.

The term "buffer" means a buffering solution or a buffering agent that stabilizes the pH of a solution. A buffer generally comprises a weak acid and its conjugate base, or a weak base and its conjugate acid. Buffering of a protein solution at or close to the optimal pH helps to ensure proper protein folding and function. The best buffer can be identified for example by measuring the circular dichroism of the protein (e.g., antibody) solution at various pHs. Circular dichrosim (CD) is one method used to determine structural changes (unfolding) of a protein (S. Beychok, "Circular dichroism of biological macromolecules," Science 154 (3754):1288-99 (1966); Kemmer and Keller, "Nonlinear least-squares data fitting in Excel spreadsheets," Nat Protoc. 5(2):267-81 (2010)). Some proteins possess the ability to act as buffers (i.e., so called "self-buffering") and therefore may not require the addition of an exogenous buffer to maintain stable pH (Gokarn et al., "Self-buffering antibody formulations," J Pharm Sci. 97(8):3051-66 (2008)). Examples of commonly used buffers are listed in Table 2. For a more complete discussion of buffers in biological solutions, see Irwin H. Segel, Biochemical Calculations ($2^{nd}$ ed. 1976), or Remington, The Science and Practice of Pharmacy 244 (Paul Beringer et al. eds., $21^{st}$ ed. 2006).

TABLE 2

| Buffering Agent | pKa | Useful pH |
| --- | --- | --- |
| Histidine | 1.82, 6.0, 9.17 | 5.5-7.4 |
| Citrate | 3.13, 4.76, 6.40 | 2.1-7.4 |
| Glycine | 2.35, 9.78 | 2.2-3.6, 8.8-10.6 |
| Acetate | 4.8 | 3.8-5.8 |
| Phosphate | 7.2 | 6.2-8.2 |
| Succinate | 4.21, 5.64 | 3.2-6.5 |
| Tris | 8.06 | 7.5-9.0 |
| HEPES | 7.48 | 6.8-8.2 |
| MOPS | 7.20 | 6.5-7.9 |
| PIPES | 6.76 | 6.1-7.5 |

The term "thermal stabilizer" means an excipient or other additive included in a biopharmaceutical formulation to provide protection to the protein against thermal degradation, denaturation, and erosion of biological activity. Generally, a thermal stabilizer helps maintain the protein (e.g., antibody) in its native conformation and prevent aggregation under conditions of thermal stress. Thermal stress may occur from freeze-thaw cycling, exposure to high temperatures, or extensive storage time. Thermal stabilizers include sugars and other carbohydrates, sugar alcohols and polyols like polyethylene glycol, and amino acids like glycine. Examples of sugars or sugar alcohols useful as a thermal stabilizer include sucrose, trehalose and mannitol.

The term "hydrophobic interaction media" means a combination of a support structure and a hydrophobic moiety, wherein the hydrophobic moiety is affixed to the support structure. The media can be in the form of chromatography media, e.g., beads or other particles held in a packed bed column format, in the form of a membrane, or in any format that can accommodate a liquid comprising a protein of interest and contaminants. Thus, support structures include agarose beads (e.g., sepharose), silica beads, cellulosic membranes, cellulosic beads, hydrophilic polymer beads, and the like. The hydrophobic moiety is the business end of the media, which binds to hydrophobic molecules and hydrophobic surfaces of proteins. The degree of hydrophobicity of the media can be controlled by selecting the hydrophobic moiety. For example, the following moieties can be affixed to media substrate to produce hydrophobic interaction media of increasing hydrophobicity, i.e., from low hydrophobicity to high hydrophobicity: ether, butyl, octyl, and phenyl. Alkyl groups may be straight chains or branched. For a review of hydrophobic interaction chromatography and media, see Kuczewski et al., "Development of a polishing step using a hydrophobic interaction membrane adsorber with a PER.C6®-derived recombinant antibody," Biotech. Bioeng. 105(2):296-305 (2010); Roettger and Ladisch, "Hydrophobic interaction chromatography," Biotechnol Adv. 7(1):15-29 (1989); Shukla and Sanchayita, "Process for purifying proteins in a hydrophobic interaction chromatography flow-through fraction," U.S. Pat. No. 7,427,659 B2, Sep. 23, 2008; and Müller and Franzreb, "Suitability of commercial hydrophobic interaction sorbents for temperature-controlled protein liquid chromatography under low salt conditions," J. Chroma. A 1260:88-96 (2012).

Hydrophobic interaction media is employed in a process known as hydrophobic interaction chromatography and is used to separate proteins of interest from product and process related contaminants. When the protein of interest is manufactured in and/or purified from host cells, the product and process related contaminants are referred to as host cell proteins (HCP). HCPs from Chinese hamster ovary (CHO) cells, a common biotherapeutic manufacturing host cell, can be referred to as CHOPs (Chinese hamster ovary proteins). In some cases, a mixture containing the protein of interest (POI) and HCPs are applied to the HIC media in a buffer designed to promote binding of hydrophobic groups in the POI to the hydrophobic moiety of the HIC medium. The POI sticks to the HIC media by binding the hydrophobic moiety, and some HCPs fail to bind and come out in the wash buffer. The POI is then eluted using a buffer that promotes dissociation of the POI from the HIC hydrophobic moiety, thereby separating the POI from unwanted HCPs.

In some cases, the HIC hydrophobic moiety preferentially binds some contaminants such as HCPs, and the POI is collected from the HIC flow-through. Here, the applicants employ HIC in a flow-through mode, wherein a population of contaminant HCPs, including an esterase activity, remain bound to the hydrophobic interaction media.

In some cases affinity chromatography designed to bind specific proteins having lipophilic attributes may be employed in lieu of or in concert with HIC. Since some esterases, such as lipases in general, or phospholipases in particular, bind to triglycerides or phospholipids, molecules that mimic those lipids may be used to capture esterases. For example, "myristoylated ADP ribosylating factor 1" (a.k.a. "myrARF1") can be used to capture a lipase and allow the POI to remain unbound and flow through. To prepare a myrARF1 affinity column, myrARF1 may be bound to Q-sepharose via N-hydroxysuccinimide activation (see Morgan et al., "Identification of phospholipase B from *Dictyostelium discoideum* reveals a new lipase family present in mammals, flies and nematodes, but not yeast," Biochem. J. 382: 441-449 (2004)).

As used herein, the term "container" is meant to include a syringe (as in a pre-filled syringe), a vial (for example a 2.5 mL glass vial for storing a biopharmaceutical formulation), or any vessel or means to contain a solid, liquid or gaseous substance. Here, the term "container" is used to refer inter alia to the vessel containing a biopharmaceutical formulation, as that term is used by the FDA and USP in its guidance on limitations for subvisible particles (United States Pharmacopeia and National Formulary (USP 33-NF 28), <788> Particulate Matter in Injections).

EXAMPLES

Example 1

Determination of Subvisible Particles in Protein Samples

The FDA requirement for subvisible particulates in parenteral drug product is ≤6,000 particles per container for particles ≥10 micrometers in diameter, and ≤600 particles per container for particles ≥25 micrometers in diameter. Presently, no specification exists for particles of less than 10 micrometers in diameter, but the FDA has requested that particles of 2 to 10 micrometers be measured.

Particles of greater than 1 micrometer in diameter were measured using HIAC light obscuration and Brightwell micro-flow imaging (MFI). HIAC combines light obscuration with laser light scattering enabling the detection and counting of particles ranging from 500 nm-350 μm in a moving fluid stream. Particles were sized based on voltage response generated in the detector and sorted into predetermined size ranges based on voltage response.

For HIAC assays, samples from a manufacturing line (GMP lots) containing a monoclonal antibody at 150 mg/mL were pooled to a total volume of 25 mL. For each pooled sample, three readings of five milliliters per sample were made. Laboratory samples of the same 150 mg/mL antibody formulation were also examined by HIAC. Samples from at least three vials (2.5 mL/vial), seven 1-mL syringes (1.14 mL/syringe), or five 2.25-mL syringes (2 mL/syringe) were pooled, and three reading of one milliliter per reading were made. HIAC 9703 and HIAC 8000A instruments (Hach Company, Loveland, Colo.) using the HRLD 400 probe (which reads up to 18,000 cumulative counts per mL) and MC05 probe (which reads up to 10,000 cumulative counts per mL) respectively, were used to make the light obscuration readings.

The MFI method used less material (i.e., 1 mL of formulation, or 1 stability vial or syringe) than HIAC light obscuration and yielded higher particulate numbers than HIAC. Since MFI is microscopy-based, that method was more sensitive to the translucent protein particulates and was able to differentiate silicone oil droplets/air bubbles from protein particulates for prefilled syringe samples. MFI was conducted on a laboratory sample containing 150 mg/mL of a monoclonal antibody (as in the HIAC analyses). For MFI, one reading of one milliliter per reading was made.

Example 2

Failure of Particulate Specification

Two GMP lots of the 150 mg/mL antibody formulation were assessed for subvisible particles via HIAC light obscuration after at least six months storage at 5° C. The formulation comprised 0.02% polysorbate 20 from supplier A, and 150 mg/mL antibody. The antibody was purified from CHO cell culture using a combination of affinity capture and ion exchange chromatography. No HIC was used. The results are presented in Table 3.

TABLE 3

| LOT | Particle Size | TIME POINT (months)/ CONDITION (5° C.) | | | | 25° C. |
|---|---|---|---|---|---|---|
| | | 0 | 6 | 9 | 12 | 6 |
| 1 | ≥10 μm | 125 | 6,299 | 13,361 | 29,505 | 32,744 |
| 2 | ≥10 μm | 18 | 353 | 8,027 | 10,797 | 18,602 |

Example 3

Quality and Purity of Fatty Acid Ester Affects SVP Formation

The effect of the nature and quality of the non-ionic detergent (polysorbate 20 and polysorbate 80) on subvisible particle formation in a protein formulation was tested by formulating an antibody in either (i) polysorbate 20 from supplier A (PS20-A), (ii) polysorbate 20 from suppler B (PS20-B), or (iii) polysorbate 80 (PS80). Table 4 shows HIAC SVP (≥10 μm SVPs) data from the formulated drug substance of the following formula: 20 mM histidine (pH 5.9), 12.5 mM acetate, 0.02% non-ionic detergent (polysorbate), 5% sucrose (w/v), 25 mM arginine, and 150 mg/mL antibody, stored as 2.5 mL fill in a 5 mL Type 1 borosilicate glass vial with a West S2-F451 4432/50 GRY B2-40 stopper.

Here, formulated drug substance ("mAb1") containing polysorbate 80 showed significantly less SVP formation over time than those formulations containing polysorbate 20. Furthermore, formulations containing polysorbate 20 from supplier B (PS20-B), which is a higher grade of polysorbate 80, showed less SVP formation than those formulations containing polysorbate 20 from supplier A (PS20-A; a lower grade of polysorbate 20). A comparative analysis of PS20-A and PS20-B shows that PS20-B has 5-10% more overall esters than PS20-A, and that PS20-A has more isosorbide laurate ester than does PS20-B (FIG. 1).

TABLE 4

| LOT | NON-IONIC DETERGENT | TIME POINT (months)/ CONDITION (5° C.) | | | | 25° C. |
|---|---|---|---|---|---|---|
| | | 0 | 6 | 9 | 12 | 6 |
| 1 | PS20-A | 125 | 6,299 | 13,361 | 29,505 | 32,744 |
| 2 | PS20-A | 18 | 353 | 8,027 | 10,797 | 18,602 |
| 1 | PS20-B | 25 | 175 | NA | 1,138 | 4,221 |
| 2 | PS20-B | 8 | 108 | NA | 1,198 | 5,682 |
| 1 | PS80 | 19 | 26 | NA | 22 | 92 |

The stability of polysorbate 20 and polysorbate 80 in the 150 mg/mL antibody (mAb1) formulation containing 0.02% non-ionic detergent (polysorbate) prepared without HIC [process 3, see below and Table 8]) were compared, under the hypothesis that degradation of the fatty acid ester promotes protein instability and consequent SVP formation. The relative amounts of remaining esters (mono- and diesters) were determined by mass spectroscopy. Significant degradation of the ester components of polysorbate 20 was observed after the samples were stored at 5° C. for six months or 45° C. for two months. Less extensive degradation was observed for polysorbate 80 under the same conditions (see Table 5). These results correlate with the SVP particle formation observations.

The rates of degradation of polysorbate 20 and polysorbate 80 formulated with 150 mg/mL antibody (mAb1) (as described above for Table 5) were determined under identical conditions using mass spectroscopy to measure relative amounts of free fatty acids and fatty acid esters. Percent ester degradation was determined using the following formula:

$$\% \text{ Ester Degradation} = \frac{\% POE \text{ esters at } T0 - \% POE \text{ esters at } T1}{\% POE \text{ esters at } T0,} \quad \text{Equation 1}$$

wherein T0=time zero, T1=time at experimental condition (i.e., 2 months at 45° C.; 6 months at 5° C.), and POE=polyoxyethylene. Table 6 shows percent degradation of polysorbate 20 and polysorbate 80 in 150 mg/mL antibody formulations. The degradation rate of polysorbate 80 was consistently lower for mAb1 (but not for all antibodies tested) than the degradation rate of polysorbate 20 in otherwise identical antibody formulations. (MAb3 formulations manufactured without HIC showed greater PS80 degradation than PS20 degradation.)

TABLE 5

| Detergent/Chemical | | Conditions (percent remaining esters) | | |
|---|---|---|---|---|
| entity | | Time zero | 6 months at 5° C. | 2 months at 45° C. |
| PS20 | Monoester | 100% | 60% | 30% |
| | Diester | 100% | 30% | 10% |
| PS80 | Monoester | 100% | 80% | 35% |
| | Diester | 100% | 75% | 25% |

TABLE 6

| | | Percent Ester Degradation | |
|---|---|---|---|
| Polyoxyethylene ester | Time zero | 6 months at 5° C. | 2 months at 45° C. |
| Polysorbate 20 | 0% | 22% | 63% |
| Polysorbate 80 | 0% | 13% | 47% |

Example 4

Polysorbate 20 Degradation Activity

To determine the etiological agent responsible for polysorbate 20 degradation, the buffered antibody (150 mg/mL) was separated into two fractions by 10 kDa filtration: a protein fraction, and a buffer fraction. These two fractions, as well as intact buffered antibody, were spiked with 0.2% (w/v) of super refined polysorbate 20 (PS20-B) and stressed at 45° C. for up to 14 days. The study showed (Table 7, part A, columns 1-2) that the protein fraction, not the buffer fraction, had an effect on the degradation of sorbitan laurate (i.e., the major component of polysorbate 20), and that the degradation of polysorbate 20 was correlated with the concentration of the antibody (Table 7, part B, columns 3-4).

TABLE 7

| | part A | part B | |
|---|---|---|---|
| Fraction | % ester remaining (14 days at 45° C.) | Antibody concentration (mg/mL) | % ester remaining (12 days at 45° C.) |
| Drug substance | 75% | 150 | 82% |
| Protein Fraction | 75% | 75 | 92% |
| Buffer Fraction | 100% | 25 | 98% |

Example 5

Hydrophobic Interaction Chromatography

Antibody was produced in a CHO cell host and purified using one of two processes (see Table 8). In one case, the antibody was purified using ion exchangers as polishing steps (capture step, ion exchange 1, ion exchange 2; "Process 3"). In the other case, one of the polishing steps used to purify the antibody was hydrophobic interaction chromatography as an additional polishing step (capture step, ion exchange, hydrophobic interaction; "Process 6"). The antibody, purified by either process 3 or process 6, was formulated at 150 mg/mL in 20 mM histidine (pH 5.9), 12.5 mM acetate, 5% sucrose, 25 mM arginine, and 0.02% polysorbate 20, and subjected to forced degradation at 45° C. for up to 14 days. At day 14, about 98% of the sorbitan laurate (i.e., intact ester) remained in the formulation containing the antibody purified using process 6, whereas only about 28% of the sorbitan laurate remained in the formulation containing the antibody purified using process 3. Therefore, the hydrophobic interaction chromatography (HIC) step likely removed an activity contributing to polysorbate degradation.

TABLE 8

| Process No. | Purification Steps | Percent Intact Polysorbate 20 |
|---|---|---|
| 1 | Protein A affinity capture (PA) | 54% |
| 2 | PA > cation exchange (CEX) | 25% |
| 3 | PA > CEX > anion exchange (AEX) | 86% |
| 4 | PA > CEX > hydrophobic interaction (HIC) | 90% |
| 5 | PA > AEX | 83% |
| 6 | PA > AEX > HIC | 92% |

The role of bulk process steps in removing the putative polysorbate degradation factor (putative esterase activity) was evaluated. Antibody produced from CHO cells was subjected to sequential purification steps, and the stability of polysorbate 20 was assessed at each step. The results from one set of experiments are presented in Table 8, which reports on the percent intact polysorbate 20 at each step or sequence of steps. Percent intact polysorbate 20 is predicted to be inversely proportional to the amount of contaminant esterase activity.

Multiple different antibodies were tested for an associated polysorbate degrading activity (esterase) and the effect of HIC on that activity. In each case, polysorbate 20 degradation activity was detected, and that activity was virtually ablated by the incorporation of a HIC purification step (Table 9).

TABLE 9

| Antibody | HIC or no HIC | PS20 Degradation at Day 15 |
|---|---|---|
| mAb1 (IgG4) | No HIC | 72% |
| mAb1 (IgG4) | HIC | 2.0% |
| mAb2 (IgG1) | No HIC | 41% |
| mAb2 (IgG1) | HIC | 2.0% |
| mAb3 (IgG4) | No HIC | 40% |
| mAb3 (IgG4) | HIC | 5.0% |
| mAb4 (IgG4) | No HIC | ND |
| mAb4 (IgG4) | HIC | 1.0% |

TABLE 10

| Purification Process | Surfactant | Time Point (months)/condition (5° C.) | | | | | | 25° C. |
|---|---|---|---|---|---|---|---|---|
| | | 0 | 6 | 12 | 18 | 24 | 36 | 6 |
| HIC used | PS20-A | 129 | 189 | 140 | NR | 178 | NR | 136 |
| No HIC | PS20-A | 35 | 769 | 1,342 | NR | 14,346 | NR | 1,951 |
| No HIC | PS20-B | 125 | 401 | 297 | 224 | NA | NA | 1,050 |

The role of HIC in subvisible particle formation was explored. Without meaning to be limited by theory, we hypothesized that the stability of the non-ionic detergent in a protein (e.g., antibody) formulation is directly correlated to the formation of subvisible particles. Loss of surfactant activity may allow protein to aggregate and form subvisible particles. Additionally or alternatively, the fatty acids released by the degrading sorbitan fatty acid esters may also contribute to subvisible particle formation as immiscible fatty acid droplets. Therefore, levels of subvisible particles ≥10 micrometers in diameter were counted in drug substance (150 mg/mL antibody in 20 mM histidine (pH 5.9), 12.5 mM acetate, 5% sucrose, 25 mM arginine, and 0.02% polysorbate 20) produced with HIC (e.g., process 6) or without HIC (e.g., process 3). The results (presented in Table 10) show that the application of a HIC step significantly reduced the formation of SVPs in the drug substance (on the order of ten-fold less), even when the lower quality PS20-A is used.

Example 6

Polysorbate Degradation Assay

Degradation of polysorbate 20 was examined using one or more of several methods. The first method employed an enzymatic colorimetric assay to quantify non-esterified fatty acids (NEFA). The NEFA-HR(2) kit (Wako Diagnostics, Richmond, Va.) was used to detect fatty acids in formulated drug substance containing polysorbate. Briefly, the samples were combined with ATP and coenzyme A (CoA) in the presence of acyl-CoA synthetase (ACS). Available (free) fatty acids reacted with the CoA to form acyl-CoA. The acyl-CoA product was reacted with oxygen and acyl-CoA oxidase to produce trans-2,3-dehydroacyl-CoA and hydrogen peroxide. Peroxidase catalyzed the reaction of the hydrogen peroxide with 4-aminoantipyrine and 3-methyl-N-ethyl-N-(β-hydroxyethyl)-aniline to form a blue purple pigment (maximum absorbance at 550 nm). The amount of NEFA in the sample is proportional to the amount of pigment. For a detailed description of the NEFA colorimetric assay, see Duncombe, "The Colorimetric Micro-Determination of Non-Esterified Fatty Acids in Plasma," Clin Chim Acta. 9:122-5 (1964); Itaya and Ui, "Colorimetric Determination of Free Fatty Acids in Biological Fluids," J. Lipid Res. 6:16-20 (1965); Novak, M., "Colorimetric Ultramicro Method for the Determination of Free Fatty Acids," J. Lipid Res. 6:431-3 (1965); and Elphick, M. C., "Modified Colorimetric Ultramicro Method for Estimating NEFA in Serum," J. Clin. Pathol. 21(5):567-70 (1968).

The test sample containing the protein of interest (and putative host cell protein contaminant) was applied to a 10 kDa molecular weight cut-off filter. The retentate was recovered in 10 mM histidine (pH 6.0) at greater than 100 g/L protein and spiked with polysorbate 20 to give a test sample of 100 g/L protein, 0.8% (w/v) polysorbate 20, 10 mM histidine, pH 6.0 ($t_{initial}$). The test sample was subjected to 45° C. for 44 hours ($t_{final}$). Some samples were spiked with oleic acid to evaluate the recovery efficiency of NEFA in the samples. Percent polysorbate degradation was calculated as follows:

$$\frac{[NEFA]t_{final} - [NEFA]t_{initial}}{[polysorbate] - [NEFA]t_{final}} \times 100\% \qquad \text{Equation 2}$$

The second method for determining polysorbate degradation was based on mass spectroscopy. Using LC/MS analysis, this assay allowed the measurement and comparison of the initial percentage of esters and remaining percentage of esters in polysorbates after incubation at 45° C. at different time points. MAb1 produced according to process 6 (without HIC and with PS degradation activity) and mAb1 produced according to process 3 (with HIC step and without PS degradation activity) (see Examples 3 and 5, and Table 8) were included as negative and positive controls, respectively.

Briefly, 15 mg of antibody sample (on the order of 5-10 mg/mL, or 7 mg/mL±1.5 mg/mL) was applied to an ultra-filter (Amicon Ultra 50K, Millipore, Billerica, Mass.) and centrifuged at 14,000×g for 15 minutes or until the remaining volume was slightly below the 100 μL marking on the device. 1 μL of 10% polysorbate was added into the spin filter with the concentrated protein followed with vortexing. The sample was recovered by inverted centrifugation for 5 minutes at 1000 g to recover the full volume in the collection tube.

The recovered volume was measured and the concentration of polysorbate calculated. 1 μL of each recovered sample was and diluted 100-fold in a separate tube, and the protein concentration measured with Nanodrop 1000 (Thermo Fisher Scientific, Inc., Wilmington, Del.). The samples were then diluted in histidine buffer (10 mM, pH 6.0) and polysorbate stock to achieve 150 mg/mL protein concentration and 0.2% (w/w) polysorbate concentration.

Time zero (T0) sample (2 μL) was reserved from each sample and stored at −80° C. until used. Samples to be tested were sealed under argon and incubated at 45° C. to induce degradation, and removed for testing at the prescribed time points. 2 μL was taken from each of the samples at each time point and diluted with water to 100 μL. Each diluted time point sample was stored at −80° C. if storage. After collection of each time point, the head space of the sample tube was filled with argon gas, the sample container resealed, and the sample returned to the incubator to resume incubation.

The time point samples were analyzed using an anion exchange column (Oasis MAX column, 30 μm, 2.1 mm×20 mm; Waters Corporation, Milford, Mass.) followed at t=5 minutes with reverse phase chromatography (ACQUITY UPLC® BEH 130 C4 column, 1.7 μm, 2.1 mm×50 mm; Waters Corporation, Milford, Mass.). The reverse phase output was connected to a mass spectrometer (Thermo Q-Exactive mass spectrometer; Thermo Fisher Scientific, Inc., Wilmington, Del.). The chromatographic conditions are described in Table 11.

The system was equilibrated with 99% mobile phase A (0.1% formic acid in water) at a flow rate of 0.1 mL/minute for 40 minutes prior to first injection. Water was used as a blank injection. The mass spectrometer parameters were as follows: mass range 150-2000 m/z; heater temperature at 250° C.; voltage 3.8 kv; sheath gas 40; auxiliary gas 10; capillary temperature 350° C.; and S-lens 50. When mass spectrometry-based identification was not necessary, charged aerosol detection (CAD) was used an analytical flow rate and a desolvation temperature at 100° C. (Lisa et al., "Quantitation of triacylglycerols from plant oils using charged aerosol detection with gradient compensation," J Chromatogr A. 1176(1-2):135-42 (2007); Plante et al., "The use of charged aerosol detection with HPLC for the measurement of lipids," Methods Mol Biol. 579:469-82 (2009)).

TABLE 11

| UPLC System | Waters ACQUITY UPLC I-Class/Dionex UltiMate 3000 |
|---|---|
| Mobile Phase | A: 0.1% formic acid in water B: 0.1% formic acid in acetonitrile |
| Column | Waters Oasis ® MAC 30 μm, 2.1 × 20 mm, Part No. 186002052 ACQUITY UPLC ® BEH130 C4 column, 1.7 μm, 2.1 mm × 50 mm from Waters, Part No. 186004496. |
| Column Temperature | 40° C. ± 1° C. |
| Autosampler Temperature | 5° C. ± 2° C. |
| Injection Volume | 20.0 μL |

| | Time (minute) | % A | % B | Flow (μL/minute) | Curve |
|---|---|---|---|---|---|
| Gradient | Initial | 99.0 | 1.0 | 100 | Initial |
| | 1.0 | 99.0 | 1.0 | 100 | Linear |
| | 5.0 | 85.0 | 15.0 | 100 | Linear |
| | 40.0 | 1.0 | 99.0 | 100 | Linear |
| | 45.0 | 1.0 | 99.0 | 100 | Linear |
| | 45.1 | 99.0 | 1.0 | 100 | Linear |
| | 50.0 | 99.0 | 1.0 | 100 | Linear |

To estimate the total amount of polyoxyethylene (POE), the mass chromatogram was extracted using the 300-800 m/z range to avoid interference from degraded proteins, and the cluster of peaks from about 8-15 minutes was integrated. For CAD chromatograms, the first cluster of POE peaks was directly integrated from about 8-15 minutes (again, retention time may shift slightly). When there were other species co-eluting with the POE, the baseline was adjusted to minimize their impact on the peak area.

To estimate the total amount of POE esters, the mass chromatogram was extracted using the 300-2000 m/z range, and the cluster of peaks from about 17-40 minutes was integrated. For the CAD chromatograms, the POE esters peak cluster was directly integrated from about 17-40 minutes.

Percentage of POE esters was calculated according to Equation 3:

$$\frac{POE \text{ esters peak area}}{POE \text{ esters peak area} + POE \text{ area}} \times 100\% \qquad \text{Equation 3}$$

Percentage of remaining POE esters was calculated according to Equation 4:

$$\frac{\%POE \text{ esters at } tn}{\%POE \text{ esters at } t0}, \qquad \text{Equation 4}$$

wherein n=2, 4, or 10 days

Example 7

Lipase and Lipase Inhibitors

Polysorbate degradation activity was followed during HIC purification of an exemplar antibody produced in CHO cell culture. Partially purified CHO cell extract was applied to HIC (phenyl-sepharose). The flow-through, which contained almost all of the antibody, was collected and analyzed for polysorbate degradation activity. No polysorbate degradation activity was observed in this flow-through fraction. The HIC bound fraction was stripped from the HIC media and subsequently subjected to 100 kDa cut-off ultrafiltration/diafiltration. The unfiltered stripped fraction contained 9.9% polysorbate degradation activity, the filter permeate contained 1.3% polysorbate degradation activity and 5% antibody yield, and the filter retentate contained 7.4% polysorbate degradation activity and 95% antibody yield.

TABLE 12

| | Percent Reduction in Polysorbate 20 Degradation (concentration of lipase inhibitor) | | | |
|---|---|---|---|---|
| Lipase Inhibitor | 0 mM (control) | 0.001 mM | 0.01 mM | 0.1 mM |
| Orlistat | 0% | 0% | 27.8% | 67% |
| Diethylumbelliferyl phosphate | 0% | 48% | 100% | >95% |
| URB602 | 0% | 0% | 20% | 0% |
| 2-Butoxyphenyl boronic acid | 0% | 0% | 28% | 0% |

Whether the polysorbate degrading activity is a lipase was tested by combining a lipase inhibitor with the polysorbate degrading activity fraction spiked with polysorbate 20. Table 12 presents the data showing a reduction of polysorbate degrading activity due to lipase inhibitor relative to the control (antibody with associated polysorbate degrading activity plus polysorbate 20 without lipase inhibitor). Lipase inhibitors reduced or eliminated the polysorbate degradation activity associated with the antibody.

Example 8

Putative Phospholipase B-Like 2 Activity

A CHO-produced recombinant antibody HIC strip fraction (not the flow-through), which contained the polysorbate degradation activity, was subjected to additional HIC in bind/elution mode, wherein the antibody was eluted with a shallow gradient. Elution fractions were tested for PS20 degradation activity and those fractions having that activity were subjected to (i) intact mass spec, (ii) native size exclusion chromatography UV analysis (SEC-UV), and (iii) tryptic digestion followed with LC-MS and proteomic search analysis. Intact mass spec of reverse phase liquid chromatography fractions revealed an unknown species in hydrophobic fraction L8 (the most hydrophobic fraction). Formulated antibody samples containing polysorbate 20 and spiked with L8 (1:100) showed 20% polysorbate degradation by day eight. Antibody monomer and free light chain were detected in less hydrophobic fractions L3-L7, as well as L8. Antibody dimer was detected in fractions L5-L8.

HIC strip fractions L3-L9 were subjected to SEC-UV under native conditions. Fraction L8 separated into three major peaks coming off first, and two minor peaks coming off later and representing smaller species. The first peak off the column contained antibody dimer and other oligomers. The second peak contained antibody monomer. The third peak contained the species having polysorbate degradation activity. Thus, the degradation activity is separable from the antibody and is of smaller molecular rotation than the antibody monomer.

HIC fraction L8 was also subjected to shotgun proteomics analysis. Briefly, the L8 fraction was sequentially (i) retained on a 10 kDa filter, (ii) reconstituted in 6M guanidine-HCl, 100 mM Tris-HCl, pH 7.5, (iii) treated for 30 minutes at 50° C. in 10 mM Tris(2-carboxythyl)phosphine hydrochloride) (TCEP) followed by 30 minutes in the dark at room temperature in 20 mM indole-3-acetic acid (IAA), (iv) diluted eight-fold and adding trypsin at 1 part trypsin to 20 parts sample and incubated at 37° C. for four hours, and then (v) subjected to LC-MS/MS analysis. Proteomic searching of the resultant peptide sequences revealed five proteins associated with L8: (i) putative phospholipase B-like 2 (representing 15% of the peak fraction), (ii) peroxiredoxin-1, (iii) heat shock 27 kDa protein 1, (iv) anaphase-promoting complex subunit 1, and (v) U3 small ribonucleoprotein protein MPP10. joseph The amount of polysorbate degradation activity correlated with the abundance of phospholipase B-like 2 protein (PLBL2) present. At various purification steps, the amount of PLBL2 was determined via nanoLC-MS or LC-MS and the rate of polysorbate degradation (PS20 spiked fractions) was determined. The abundance of PLBL2 was calculated based on the ratio of peptide intensity from the lipase and drug substance (i.e., antibody). The results are presented in FIG. 2 and Table 13.

TABLE 13

| Fraction | Percent PS20 Degradation | Relative Amount PLBL2 (ppm)[2] |
|---|---|---|
| ProA pool | 69.02% | 991 |
| CEX pool | 55.24% | 403 |
| AEX pool | 12.85% | 84 |
| HIC pool | 8.67% | 0 |
| HIC pool 2 | 10.96% | 0 |
| HIC strip | 83.75% | 1384 |
| mAb1 process 3 (example 5) | 4.60% | 0 |
| mAb1 process 6 (example 5)[1] | 29.12% | 92 |

[1]Degradation rate adjusted by concentration.
[2]Abundance of phopholipase calculated based on the ratio of peptide intensity from the lipase and drug substance.

---

The invention claimed is:

1. A process for manufacturing a formulated drug substance comprising an antibody produced by a host cell, the process comprising:
in a first purification step, separating the antibody and a phospholipase B-like 2 protein (PLBL2) from the host cell to obtain a composition comprising the antibody and the PLBL2, wherein the first purification step includes protein affinity capture;
in a second purification step, separating the antibody from the PLBL2 by contacting the composition with one of a hydrophobic interaction chromatography (HIC) resin or an HIC membrane; and
after the second purification step, combining the antibody and a fatty acid ester to make the formulated drug substance, wherein the formulated drug substance is essentially free of subvisible particles.

2. The process of claim 1, wherein the first purification step further includes an ion exchange process.

3. The process of claim 1, wherein the one of the HIC resin or the HIC membrane preferentially binds the PLBL2 and does not bind the antibody.

4. The process of claim 1, wherein the one of the HIC resin or the HIC membrane comprises a hydrophobic moiety selected from the group consisting of a phenyl, ether, butyl, octyl, straight chain alkane, branch chain alkane, 8-carbon alkane, and 18-carbon alkane.

5. The process of claim 1, further comprising:
concentrating the antibody after separating the antibody from the PLBL2.

6. The process of claim 5, further comprising:
combining a buffer and a thermal stabilizer with the concentrated antibody.

7. The process of claim 1, further comprising:
storing the formulated drug substance at 5° C. for at least 6 months.

8. The process of claim 1, further comprising:
disposing a volume of the formulated drug substance in a container, wherein the volume of the formulated drug substance contains less than 400 particles having a diameter of ≥10 microns.

9. The process of claim 8, wherein the container contains less than 10,000 particles having a diameter of ≥2 microns.

10. The process of claim 1, wherein the antibody is a recombinant human monoclonal antibody.

11. The process of claim 1, wherein the PLBL2 comprises the amino acid sequence of SEQ ID NO:1.

12. The process of claim 1, wherein the fatty acid ester is a polyoxyethylene (20) sorbitan ester.

13. The process of claim 12, wherein the polyoxyethylene (20) sorbitan ester is polysorbate 20 or polysorbate 80.

14. The process of claim 1, wherein the concentration of the antibody in the formulated drug substance is at least 30 mg/mL.

15. The process of claim 1, further comprising storing the formulated drug substance at 5° C. for at least 6 months, after which the formulated drug substance includes less than 400 particles having an average mean diameter of ten microns or more.

16. The process of claim 1, further comprising storing the formulated drug substance at 5° C. for at least 6 months, after which the formulated drug substance includes less than 10,000 particles having an average mean diameter of 2 microns or more.

17. A process for manufacturing a formulated drug substance comprising an IgG antibody produced by a host cell, the process comprising:
in a first purification step, separating the IgG antibody and a phospholipase B-like 2 protein (PLBL2) from the host cell to obtain a composition comprising the IgG antibody and the PLBL2, wherein the first purification step comprises performing protein affinity capture and an ion exchange process;
in a second purification step, contacting the composition with one of a hydrophobic interaction chromatography (HIC) resin or an HIC membrane to preferentially bind the PLBL2 without binding the IgG antibody;
after the second purification step, combining the IgG antibody, a fatty acid ester, a buffer, and a thermal stabilizer to make the formulated drug substance; and
storing the formulated drug substance at 5° C. for at least 6 months, after which the formulated drug substance includes less than 400 particles having an average mean diameter of ten microns or more.

18. The process of claim 17, wherein after storage the formulated drug substance includes less than 10,000 particles having an average mean diameter of 2 microns or more.

19. The process of claim 17, wherein the ion exchange process comprises performing anion exchange chromatography.

20. The process of claim 17, wherein the ion exchange process comprises performing cation exchange chromatography.

21. The process of claim 17, wherein the host cell is a Chinese hamster ovary cell.

* * * * *

SEQUENCE LISTING

```
<160> NUMBER OF SEQ ID NOS: 31

<210> SEQ ID NO 1
<211> LENGTH: 17
<212> TYPE: PRT
<213> ORGANISM: Cricetulus griseus

<400> SEQUENCE: 1

Asp Leu Leu Val Ala His Asn Thr Trp Asn Ser Tyr Gln Asn Met Leu
1               5                   10                  15

Arg

<210> SEQ ID NO 2
<211> LENGTH: 22
<212> TYPE: PRT
<213> ORGANISM: Cricetulus griseus

<400> SEQUENCE: 2

Leu Ile Arg Tyr Asn Asn Phe Leu His Asp Pro Leu Ser Leu Cys Glu
1               5                   10                  15

Ala Cys Ile Pro Lys Pro
            20

<210> SEQ ID NO 3
<211> LENGTH: 12
<212> TYPE: PRT
<213> ORGANISM: Cricetulus griseus

<400> SEQUENCE: 3

Ser Val Leu Leu Asp Ala Ala Ser Gly Gln Leu Arg
```

<210> SEQ ID NO 4
<211> LENGTH: 13
<212> TYPE: PRT
<213> ORGANISM: Cricetulus griseus

<400> SEQUENCE: 4

Asp Gln Ser Leu Val Glu Asp Met Asn Ser Met Val Arg
1               5                   10

<210> SEQ ID NO 5
<211> LENGTH: 17
<212> TYPE: PRT
<213> ORGANISM: Cricetulus griseus

<400> SEQUENCE: 5

Gln Phe Asn Ser Gly Thr Tyr Asn Asn Gln Trp Met Ile Val Asp Tyr
1               5                   10                  15

Lys

<210> SEQ ID NO 6
<211> LENGTH: 20
<212> TYPE: PRT
<213> ORGANISM: Cricetulus griseus

<400> SEQUENCE: 6

Gln Gly Pro Gln Glu Ala Tyr Pro Leu Ile Ala Gly Asn Asn Leu Val
1               5                   10                  15

Phe Ser Ser Tyr
            20

<210> SEQ ID NO 7
<211> LENGTH: 19
<212> TYPE: PRT
<213> ORGANISM: Cricetulus griseus

<400> SEQUENCE: 7

Ser Met Leu His Met Gly Gln Pro Asp Leu Trp Thr Phe Ser Pro Ile
1               5                   10                  15

Ser Val Pro

<210> SEQ ID NO 8
<211> LENGTH: 21
<212> TYPE: PRT
<213> ORGANISM: Cricetulus griseus

<400> SEQUENCE: 8

Tyr Asn Asn Phe Leu His Asp Pro Leu Ser Leu Cys Glu Ala Cys Ile
1               5                   10                  15

Pro Lys Pro Asn Ala
            20

<210> SEQ ID NO 9
<211> LENGTH: 13
<212> TYPE: PRT
<213> ORGANISM: Cricetulus griseus

<400> SEQUENCE: 9

Leu Ala Leu Asp Gly Ala Thr Trp Ala Asp Ile Phe Lys
1               5                   10

```
<210> SEQ ID NO 10
<211> LENGTH: 13
<212> TYPE: PRT
<213> ORGANISM: Cricetulus griseus

<400> SEQUENCE: 10

Leu Ser Leu Gly Ser Gly Ser Cys Ser Ala Ile Ile Lys
1               5                   10

<210> SEQ ID NO 11
<211> LENGTH: 13
<212> TYPE: PRT
<213> ORGANISM: Cricetulus griseus

<400> SEQUENCE: 11

Tyr Val Gln Pro Gln Gly Cys Val Leu Glu Trp Ile Arg
1               5                   10

<210> SEQ ID NO 12
<211> LENGTH: 19
<212> TYPE: PRT
<213> ORGANISM: Cricetulus griseus

<400> SEQUENCE: 12

Arg Met Ser Met Leu Ala Ala Ser Gly Pro Thr Trp Asp Gln Leu Pro
1               5                   10                  15

Pro Phe Gln

<210> SEQ ID NO 13
<211> LENGTH: 12
<212> TYPE: PRT
<213> ORGANISM: Cricetulus griseus

<400> SEQUENCE: 13

Ser Phe Leu Glu Ile Asn Leu Glu Trp Met Gln Arg
1               5                   10

<210> SEQ ID NO 14
<211> LENGTH: 22
<212> TYPE: PRT
<213> ORGANISM: Cricetulus griseus

<400> SEQUENCE: 14

Val Leu Thr Ile Leu Glu Gln Ile Pro Gly Met Val Val Val Ala Asp
1               5                   10                  15

Ala Asp Lys Thr Glu Asp
                20

<210> SEQ ID NO 15
<211> LENGTH: 14
<212> TYPE: PRT
<213> ORGANISM: Cricetulus griseus

<400> SEQUENCE: 15

Val Arg Ser Val Leu Leu Asp Ala Ala Ser Gly Gln Leu Arg
1               5                   10

<210> SEQ ID NO 16
<211> LENGTH: 16
<212> TYPE: PRT
<213> ORGANISM: Cricetulus griseus

<400> SEQUENCE: 16

Leu Thr Leu Leu Gln Leu Lys Gly Leu Glu Asp Ser Tyr Glu Gly Arg
```

<210> SEQ ID NO 17
<211> LENGTH: 18
<212> TYPE: PRT
<213> ORGANISM: Cricetulus griseus

<400> SEQUENCE: 17

Met Ser Met Leu Ala Ala Ser Gly Pro Thr Trp Asp Gln Leu Pro Pro
1               5                   10                  15

Phe Gln

<210> SEQ ID NO 18
<211> LENGTH: 9
<212> TYPE: PRT
<213> ORGANISM: Cricetulus griseus

<400> SEQUENCE: 18

Val Thr Ser Phe Ser Leu Ala Lys Arg
1               5

<210> SEQ ID NO 19
<211> LENGTH: 9
<212> TYPE: PRT
<213> ORGANISM: Cricetulus griseus

<400> SEQUENCE: 19

Gln Asn Leu Asp Pro Pro Val Ser Arg
1               5

<210> SEQ ID NO 20
<211> LENGTH: 10
<212> TYPE: PRT
<213> ORGANISM: Cricetulus griseus

<400> SEQUENCE: 20

Ile Ile Lys Lys Tyr Gln Leu Gln Phe Arg
1               5                   10

<210> SEQ ID NO 21
<211> LENGTH: 19
<212> TYPE: PRT
<213> ORGANISM: Cricetulus griseus

<400> SEQUENCE: 21

Ala Gln Ile Phe Gln Arg Asp Gln Ser Leu Val Glu Asp Met Asn Ser
1               5                   10                  15

Met Val Arg

<210> SEQ ID NO 22
<211> LENGTH: 22
<212> TYPE: PRT
<213> ORGANISM: Cricetulus griseus

<400> SEQUENCE: 22

Leu Ile Arg Tyr Asn Asn Phe Leu His Asp Pro Leu Ser Leu Cys Glu
1               5                   10                  15

Ala Cys Ile Pro Lys Pro
            20

<210> SEQ ID NO 23
<211> LENGTH: 12
<212> TYPE: PRT

<213> ORGANISM: Cricetulus griseus

<400> SEQUENCE: 23

Ser Val Leu Leu Asp Ala Ala Ser Gly Gln Leu Arg
1               5                   10

<210> SEQ ID NO 24
<211> LENGTH: 13
<212> TYPE: PRT
<213> ORGANISM: Cricetulus griseus

<400> SEQUENCE: 24

Asp Gln Ser Leu Val Glu Asp Met Asn Ser Met Val Arg
1               5                   10

<210> SEQ ID NO 25
<211> LENGTH: 17
<212> TYPE: PRT
<213> ORGANISM: Cricetulus griseus

<400> SEQUENCE: 25

Asp Leu Leu Val Ala His Asn Thr Trp Asn Ser Tyr Gln Asn Met Leu
1               5                   10                  15

Arg

<210> SEQ ID NO 26
<211> LENGTH: 21
<212> TYPE: PRT
<213> ORGANISM: Cricetulus griseus

<400> SEQUENCE: 26

Tyr Asn Asn Phe Leu His Asp Pro Leu Ser Leu Cys Glu Ala Cys Ile
1               5                   10                  15

Pro Lys Pro Asn Ala
            20

<210> SEQ ID NO 27
<211> LENGTH: 19
<212> TYPE: PRT
<213> ORGANISM: Cricetulus griseus

<400> SEQUENCE: 27

Arg Met Ser Met Leu Ala Ala Ser Gly Pro Thr Trp Asp Gln Leu Pro
1               5                   10                  15

Pro Phe Gln

<210> SEQ ID NO 28
<211> LENGTH: 19
<212> TYPE: PRT
<213> ORGANISM: Cricetulus griseus

<400> SEQUENCE: 28

Ser Met Leu His Met Gly Gln Pro Asp Leu Trp Thr Phe Ser Pro Ile
1               5                   10                  15

Ser Val Pro

<210> SEQ ID NO 29
<211> LENGTH: 18
<212> TYPE: PRT
<213> ORGANISM: Cricetulus griseus

<400> SEQUENCE: 29

```
Met Ser Met Leu Ala Ala Ser Gly Pro Thr Trp Asp Gln Leu Pro Pro
1               5                   10                  15

Phe Gln

<210> SEQ ID NO 30
<211> LENGTH: 14
<212> TYPE: PRT
<213> ORGANISM: Cricetulus griseus

<400> SEQUENCE: 30

Val Arg Ser Val Leu Leu Asp Ala Ala Ser Gly Gln Leu Arg
1               5                   10

<210> SEQ ID NO 31
<211> LENGTH: 9
<212> TYPE: PRT
<213> ORGANISM: Cricetulus griseus

<400> SEQUENCE: 31

Gln Asn Leu Asp Pro Pro Val Ser Arg
1               5
```